(12) United States Patent
Brown et al.

(10) Patent No.: US 9,011,949 B2
(45) Date of Patent: Apr. 21, 2015

(54) METHODS AND COMPOSITIONS FOR CONSUMABLES

(71) Applicant: Impossible Foods Inc., Redwood City, CA (US)

(72) Inventors: Patrick O'Reilly Brown, Stanford, CA (US); Monte Casino, San Bruno, CA (US); Lynn S. Voccola, Pacifica, CA (US); Ranjani Varadan, Fremont, CA (US)

(73) Assignee: Impossible Foods Inc., Redwood City, CA (US)

( * ) Notice: Subject to any disclaimer, the term of this patent is extended or adjusted under 35 U.S.C. 154(b) by 0 days.

(21) Appl. No.: 14/152,531

(22) Filed: Jan. 10, 2014

(65) Prior Publication Data

US 2014/0127358 A1   May 8, 2014

Related U.S. Application Data

(63) Continuation of application No. PCT/US2012/046552, filed on Jul. 12, 2012.

(60) Provisional application No. 61/507,096, filed on Jul. 12, 2011.

(51) Int. Cl.
| | | |
|---|---|---|
| A23C 20/02 | (2006.01) | |
| A23C 9/12 | (2006.01) | |
| A23K 1/16 | (2006.01) | |

(Continued)

(52) U.S. Cl.
CPC ............... *A23C 20/02* (2013.01); *A23K 1/1631* (2013.01); *A23K 1/1656* (2013.01); *A23K 1/1866* (2013.01); *A23C 20/005* (2013.01); *C12Y 203/02013* (2013.01)

(58) Field of Classification Search
CPC .... A23C 20/005; A23C 20/02; A23C 11/103; A23C 20/00; A23C 19/055; A23C 19/093; A23C 20/025; C12Y 203/02013; A23L 1/052; A23L 1/3252; A23L 1/2005; A23L 1/3149; A23J 3/34; C12N 9/1044; A23V 2250/5488
USPC .......... 426/63, 582, 56, 46, 634, 59, 598, 629
See application file for complete search history.

(56) References Cited

U.S. PATENT DOCUMENTS

| | | | |
|---|---|---|---|
| 3,658,550 | A | 4/1972 | Hawley |
| 3,693,533 | A | 9/1972 | Liepa |

(Continued)

FOREIGN PATENT DOCUMENTS

| | | | |
|---|---|---|---|
| CN | 1252231 A | 5/2000 | |
| CN | 1301811 A | 7/2001 | |

(Continued)

OTHER PUBLICATIONS

Homma, H. et al. Cheese-like food production from various nuts. Food Preservation Science, Japan 2009. Abstract.*

(Continued)

*Primary Examiner* — Hamid R Badr
(74) *Attorney, Agent, or Firm* — Fish & Richardson P.C.

(57) ABSTRACT

Provided herein are methods and compositions for the production of cheese replicas. Generally the cheese replicas are produced by inducing the enzymatic curdling of non-dairy milks.

30 Claims, 6 Drawing Sheets

(51) Int. Cl.
    *A23K 1/165*  (2006.01)
    *A23K 1/18*   (2006.01)
    *A23C 20/00*  (2006.01)

(56) References Cited

U.S. PATENT DOCUMENTS

| | | | |
|---|---|---|---|
| 3,966,985 A | 6/1976 | Jonas | |
| 3,973,043 A | 8/1976 | Lynn | |
| 4,045,587 A | 8/1977 | Katz et al. | |
| 4,094,997 A | 6/1978 | Aishima et al. | |
| 4,218,487 A | 8/1980 | Jaeggi | |
| 4,604,290 A | 8/1986 | Lee et al. | |
| 4,678,676 A * | 7/1987 | Ishizuka et al. | 426/573 |
| 4,994,285 A | 2/1991 | Hisano et al. | |
| 5,055,310 A * | 10/1991 | Nonaka et al. | 426/46 |
| 5,264,239 A | 11/1993 | Cornet et al. | |
| 5,597,594 A * | 1/1997 | Matsuura et al. | 426/44 |
| 5,650,554 A | 7/1997 | Moloney et al. | |
| 5,807,601 A | 9/1998 | Carpenter et al. | |
| 5,856,452 A | 1/1999 | Moloney et al. | |
| 5,922,392 A | 7/1999 | Kelly et al. | |
| 6,093,424 A | 7/2000 | Han et al. | |
| 6,146,645 A | 11/2000 | Deckers et al. | |
| 6,183,762 B1 | 2/2001 | Deckers et al. | |
| 6,210,742 B1 | 4/2001 | Deckers et al. | |
| 6,228,418 B1 | 5/2001 | Gluck et al. | |
| 6,242,036 B1 | 6/2001 | Han et al. | |
| 6,287,620 B1 | 9/2001 | Van Den Ouweland et al. | |
| 6,372,234 B1 | 4/2002 | Deckers et al. | |
| 6,372,961 B1 | 4/2002 | Tarczynski | |
| 6,379,738 B1 | 4/2002 | Dingman et al. | |
| 6,383,531 B1 | 5/2002 | Gottemoller | |
| 6,399,135 B2 | 6/2002 | Gottemoller | |
| 6,413,569 B1 | 7/2002 | Borders et al. | |
| 6,416,797 B1 | 7/2002 | Han et al. | |
| 6,420,148 B2 | 7/2002 | Yamaguchi | |
| 6,495,184 B1 | 12/2002 | Zheng et al. | |
| 6,495,187 B1 | 12/2002 | Borders et al. | |
| 6,509,453 B1 | 1/2003 | Moloney | |
| 6,582,710 B2 | 6/2003 | Deckers et al. | |
| 6,596,287 B2 | 7/2003 | Deckers et al. | |
| 6,599,513 B2 | 7/2003 | Deckers et al. | |
| 6,692,788 B1 | 2/2004 | Mottram et al. | |
| 6,761,914 B2 | 7/2004 | Deckers et al. | |
| 6,908,634 B2 | 6/2005 | Hwang | |
| 6,936,749 B1 | 8/2005 | Guy et al. | |
| 7,052,879 B2 | 5/2006 | Shaw et al. | |
| 7,332,587 B2 | 2/2008 | Moloney | |
| 7,407,786 B2 | 8/2008 | Giver et al. | |
| 7,479,472 B1 | 1/2009 | Harbury et al. | |
| 7,585,645 B2 | 9/2009 | Deckers et al. | |
| 7,622,290 B2 | 11/2009 | Brunstedt et al. | |
| 7,666,618 B2 | 2/2010 | Miasnikov et al. | |
| 7,666,628 B2 | 2/2010 | Moloney | |
| 7,674,953 B2 | 3/2010 | Mulet Salort et al. | |
| 7,709,044 B2 | 5/2010 | Ishimoto | |
| 7,807,870 B2 | 10/2010 | Geigenberger et al. | |
| 7,931,925 B2 | 4/2011 | Nielsen | |
| 8,012,732 B2 | 9/2011 | Brunstedt et al. | |
| 8,021,695 B2 | 9/2011 | Gruber et al. | |
| 8,188,415 B2 | 5/2012 | Kats et al. | |
| 8,304,522 B2 | 11/2012 | Kugitani | |
| 8,597,694 B2 | 12/2013 | Guth et al. | |
| 2001/0049132 A1 * | 12/2001 | Kringelum et al. | 435/252.4 |
| 2003/0198700 A1 | 10/2003 | Gruber | |
| 2003/0224476 A1 | 12/2003 | Chou | |
| 2004/0161513 A1 | 8/2004 | Akashe et al. | |
| 2005/0037111 A1 | 2/2005 | Berry | |
| 2006/0035003 A1 | 2/2006 | McMindes et al. | |
| 2006/0233721 A1 | 10/2006 | Tamarkin et al. | |
| 2007/0269567 A1 | 11/2007 | McMindes et al. | |
| 2007/0269571 A1 | 11/2007 | Akita et al. | |
| 2007/0269583 A1 | 11/2007 | McMindes et al. | |
| 2008/0254168 A1 | 10/2008 | Mueller et al. | |
| 2008/0268112 A1 | 10/2008 | Rolan et al. | |
| 2008/0292749 A1 | 11/2008 | Goodwins et al. | |
| 2008/0299254 A1 | 12/2008 | Kim et al. | |
| 2009/0264520 A1 | 10/2009 | Bhagat | |
| 2010/0074998 A1 | 3/2010 | Vega et al. | |
| 2010/0136201 A1 | 6/2010 | Bigeard et al. | |
| 2010/0233347 A1 | 9/2010 | Uhrhan | |
| 2010/0249560 A1 | 9/2010 | Levinson et al. | |
| 2011/0008502 A1 | 1/2011 | Hosomi et al. | |
| 2011/0064847 A1 | 3/2011 | Miwa et al. | |
| 2011/0064862 A1 | 3/2011 | McCready et al. | |
| 2011/0081386 A1 | 4/2011 | Guth et al. | |
| 2011/0081435 A1 | 4/2011 | Guth et al. | |
| 2011/0117180 A1 | 5/2011 | Yan et al. | |
| 2011/0286992 A1 | 11/2011 | Gruber et al. | |
| 2011/0288389 A9 | 11/2011 | Levinson et al. | |
| 2012/0059150 A1 | 3/2012 | Moloney et al. | |
| 2012/0093994 A1 | 4/2012 | Hsieh et al. | |

FOREIGN PATENT DOCUMENTS

| | | |
|---|---|---|
| CN | 1407108 A | 4/2003 |
| CN | 1593223 A | 3/2005 |
| CN | 1634524 A | 7/2005 |
| CN | 101138405 | 3/2008 |
| CN | 101541187 A | 9/2009 |
| CN | 101606574 A | 12/2009 |
| EP | 1166653 A2 | 1/2002 |
| EP | 0680751 | 11/2004 |
| EP | 1952695 | 8/2008 |
| JP | S 573338 | 1/1982 |
| WO | WO 93/25697 | 12/1993 |
| WO | WO 94/17673 | 8/1994 |
| WO | WO 96/17981 | 6/1996 |
| WO | WO 98/12913 | 4/1998 |
| WO | WO 98/53698 | 12/1998 |
| WO | WO 01/22829 | 4/2001 |
| WO | WO 01/22830 | 4/2001 |
| WO | WO 03/070172 | 8/2003 |
| WO | WO 2004/113543 | 12/2004 |
| WO | WO 2005/013713 | 2/2005 |
| WO | WO 2005/097059 | 10/2005 |
| WO | WO 2006/042608 | 4/2006 |
| WO | WO 2007/115899 | 10/2007 |
| WO | WO 2007/118751 | 12/2007 |
| WO | WO 2008/083117 | 7/2008 |
| WO | WO 2009/060678 | 5/2009 |
| WO | WO 2010/101625 | 9/2010 |
| WO | WO 2012/106751 | 8/2012 |
| WO | WO 2012/110797 | 8/2012 |
| WO | WO 2013/010037 | 1/2013 |
| WO | WO 2013/010042 | 1/2013 |
| WO | WO 2013/138793 | 9/2013 |

OTHER PUBLICATIONS

Gharst, G. A. 2007. Biochemical and Rheological Characteristics of Peanut Proteins Crosslinked with Microbial Transglurtaminase. A dissertation submitted to the Graduate Faculty of North Carolina State University. Raleigh NC. Abstract.*
Beuchat, L. R. et al. 1978. J. Food Sci. 43: 1109-1112.*
International Search Report and Written Opinion in International Application No. PCT/US2012/046560, mailed Dec. 14, 2012, 11 pages.
International Preliminary Report on Patentability in International Applicaton No. PCT/US2012/046560, mailed Jan. 23, 2014, 12 pages.
International Search Report and Written Opinion in International Application No. PCT/US2012/46552, mailed Nov. 19, 2012, 12 pages.
International Preliminary Report on Patentability in International Applicaton No. PCT/US2012/46552, mailed Jan. 23, 2014, 9 pages.
Ba et al., "Principles of Meat Aroma flavors and Future Prospect," *INTECH Open Science, Open Minds*, 2012, Chapter 7, 145-176.
Baek, "Process Flavors," *Handbook of Meat, Poultry and Seafood Quality*, Second Edition, 2012, Chapter 7, 91-104.
Battaglia et al., "The Enigmatic LEA Proteins and Other HydroPhilins[1][W]," *Plant Physiology*, Sep. 2008, 148:6-24.

(56) References Cited

OTHER PUBLICATIONS

Beyond Meat, posted on or before Feb. 24, 2001, accessed Jan. 7, 2014, http://beyondmeat.com, 2 pages.
Boca Bruschetta Tomato Basil Parmesan Veggie Patties Package Ingredients, posted on or before Jul. 22, 2008, accessed on Jan. 7, 2014, http://www.bocaburger.com/products/nutrition-info.aspx?product-5928360103, 1 page.
Boca Flame Grilled Meatless Burgers Package Ingredients, posted on or before Jul. 14, 2008, accessed on Jan. 7, 2014, http://www.bocaburger.com/products/nutrition-info.aspx?product=5928367321, 1 page.
Boca Original Meatless Chik'n Nuggets Package Ingredients, posted on or before Jul. 22, 2008, accessed Jan. 7, 2014, http://www.bocaburger.com/products/nutrition-info.aspx?product-5928360012, 1 page.
Boca Original Vegan Meatless Burgers Package Ingredients, posted on or before Jul. 14, 2008, accessed Jan. 7, 2014, http://www.bocaburger.com/products/nutrition-info.aspx?product=5928333445, 1 page.
Boral and Bohidar, "Effect of Ionic Strength on Surface-Selective Patch Binding-Induced Phase Separation and Coacervation in Similarly Charged Gelatin-Agar Molecular Systems," *Journal of Physical Chemistry B*, 2010, 114(37): 12027-35.
Chicago Vegan Foods, accessed on Jan. 7, 2014, http://chicagoveganfoods.com/products/teese-vegan-cheese/, 8 pages.
Daiya, Deliciously Dairy Free, "Say Cheese, Dairy-Free cheesy deliciousness," posted on or before Jan. 26, 2010, accessed Jan. 7, 2014, http://www.daiyafoods.com, 6 pages.
Dr. Cow, Natural Living & Organic Foods, "Cashew Nut Cream Cheese," posted on or before Sep. 22, 2008, accessed Jan. 7, 2014, http://www.dr-cow.com/products/cashew-nut-cream-cheese.html, 1 page.
Fantastic World Foods, "Fantastic Foods Nature's Burger (Meatless Burger Mix)," posted on or before Jan. 6, 2009, accessed on Jan. 7, 2014, http://fantasticfoods.elsstore.com/view/products/?id=8715&cid=1967, 2 pages.
Follow Your Heart Homepage, posted on or before Nov. 28, 1999, accessed Jan. 7, 2014, http://www.followyourheart.com, 3 pages.
Gardein The Ultimate Beefless Burger Package Ingredients, posted on or before 2013, accessed Jan. 7, 2014, http://gardein.com/products/beefless-burger/, 12 pages.
Gardenburger The Original Veggie Burger Package Ingredients, posted on or before Oct. 5, 2008, accessed Jan. 7, 2014, http://www.gardenburger.com/product.asp?id=11630, 1 page.
Go Veggie!, "O% Dairy. 100% Yum.," posted on or before 2013, accessed Jan. 7, 2014, http://goveggiefoods.com/our-products/dairy-free-cheese-alternative-products/, 1 page.
Gordinier, "Masters of Disguise Among Meatless Burgers," *The New York Times*, Mar. 22, 2011, accessed Jan. 7, 2014, http://www.nytimes.com/2011/03/23/dining/23meatless.html?pagewanted=all&_r=0, 5 pages.
Heme Protein Database, "Welcome to the Heme Protein Database," posted on or before Apr. 14, 2013, accessed Dec. 18, 2013, http://hemeprotein.info/heme.php, 1 page.
Ju and Kilara, "Textural Properties of Cold-set Gels Induced from Heat-denatured Whey Protein Isolates," *J. Food Science*, 1998, 63(2): 288-292.
Kraft American Singles Package Ingredients, posted on or before Jun. 27, 2012, accessed on Jan. 7, 2014, http://www.kraftrecipes.com/Products/ProductInfoDisplay.aspx?SiteId=1&Product=2100060473, 1 page.
Kung et al., "Tobacco as a Potential Food Source and Smoke Material: Nutritional Evaluation of Tobacco Leaf Protein," J. Food Sci., 1980, 45(2):320-322, 327.
Liu et al., "Intermolecular Interactions During Complex Coacervation of Pea Protein Isolate and Gum Arabic," *Journal of Agricultural and Food Chemistry*, 2010, 58:552-556.
Lugay and Kim, "Freeze alignment: A novel method for protein texturization," *Utilization of Protein Resources*, 1981, p. 177-187.
Luteness, "The Richest Source of Protein," MOSAIC, May/Jun. 1979, 39-45.
Maltais et al., "Formation of Soy Protein Isolate Cold-Set Gels: Proteins and Salt Effects," *J. Food Science*, 2005, 70 (1): C67-C73.
Morningstar Farms Garden Veggie Patties Package Ingredients, posted on or before Jun. 26, 2013, accessed Jan. 7, 2014, https://www.morningstarfarms.com/products/burgers/garden-veggie-patties, 6 pages.
Nielson, *Introduction to the Chemical Analysis of Foods*, Jones & Bartlett Publishers, 1994.
Reedy et al., "Development of a heme protein structure-electrochemical function database," *Nucleic Acids Research*, 2008, 36:307-313.
Tofutti Milk Free, "Premium Dairy Free Cheeses,", posted on or before Jun. 26, 2013, accessed Jan. 7, 2014, http://www.tofutti.com/dairy-free-cheeses/, 2 pages.
Van Den Ouweland et al., "Process Meat Flavor Development and the Maillard Reaction," In *Thermal Generation of Aromas, ACS Symposium Series*, American Chemical Society, 1989, 433-441.
VBites, "Cheezly," posted on or before 2013, accessed Jan. 7, 2014, http://www.vbitesfoods.com/meat-free/cheezly.html, 2 pages.
Welcome to Bute Island Foods, "100% Vegan Cheese—100% Tasty," posted on or before Dec. 5, 2006, accessed Jan. 7, 2014, http://www.buteisland.com, 2 pages.
Beyond Better Order page and Nutritional Facts, retrieved on Feb. 6, 2014, http://www.beyond-better.com/order.html, 8 pages.
Bute Island Foods, "Sheese," posted on or before Dec. 5, 2006, retrieved on Feb. 6, 2014, http://www.buteisland.com/a_sheese_home.htm, 26 pages.
Chicago Vegan Foods, Teese Products and Nutrition Facts, posted on or before Mar. 20, 2012, retrieved on Feb. 11, 2014, http://chicagoveganfoods.com/products/teese-vegan-cheese/, 10 pages.
Deliciously Healthy Nacheez, Products and Nutrition Facts, posted on or before Jan. 23, 2011, retrieved on Feb. 7, 2014, http://nacheez.com/, 9 pages.
Dixie Diner's Club, Cheese (Not!) Sauce Nutrition Facts, posted on or before Sep. 3, 2009, retrieved on Feb. 7, 2014, http://www.dixiediner.com/cheese-notÂ™-sauce-regular-cheese-p-69.html, 2 pages.
Door 86 Vegan Cheese, Discover a New World of Vegan Cheese and Menu, posted on or before Dec. 5, 2013, retrieved Feb. 7, 2014, http://door86vegancheese.wix.com/door-86-vegan-cheese#, 14 pages.
Dr. Cow, Natural Living & Organic Foods, "Aged Cashew & Brazil Nut Cheese," posted on or before Sep. 22, 2008, accessed Feb. 7, 2014, http://www.dr-cow.com/products/aged-cashew-brazil.html, 1 page.
Dr. Cow, Natural Living & Organic Foods, "Aged Cashew & Crystal Algae Cheese," posted on or before Sep. 22, 2008, accessed Feb. 7, 2014, http://www.dr-cow.com/products/aged-cashew-crystal.html, 1 page.
Dr. Cow, Natural Living & Organic Foods, "Aged Cashew & Dulse Cheese," posted on or before Sep. 22, 2008, accessed Feb. 7, 2014, http://www.dr-cow.com/products/aged-cashew-dulse.html, 1 page.
Dr. Cow, Natural Living & Organic Foods, "Aged Cashew & Hemp Seeds Cheese," posted on or before Sep. 22, 2008, accessed Feb. 7, 2014, http://www.dr-cow.com/products/aged-cashew-hemp.html, 1 page.
Dr. Cow, Natural Living & Organic Foods, "Aged Cashew Nut Cheese," posted on or before Sep. 22, 2008, accessed Feb. 7, 2014, http://www.dr-cow.com/products/aged-cashew-nut-cheese.html, 1 page.
Dr. Cow, Natural Living & Organic Foods, "Aged Macadamia & Hemp Seeds Cheese," posted on or before Sep. 22, 2008, accessed Feb. 7, 2014, http://www.dr-cow.com/products/aged-macadam-hemp.html, 1 page.
Dr. Cow, Natural Living & Organic Foods, "Aged Macadamia Nut Cheese," posted on or before Sep. 22, 2008, accessed Feb. 7, 2014, http://www.dr-cow.com/products/aged-macadam-nut-cheese.html, 1 page.
Follow Your Heart, Products and Nutrition Facts, posted on or before Nov. 28, 1999, accessed Feb. 7, 2014, http://www.followyourheart.com/products/, 26 pages.

(56) References Cited

OTHER PUBLICATIONS

Food for Lovers, Vegan Queso Original & Vegan Queso Mild, posted on or before Oct. 27, 2011, retrieved Feb. 7, 2014, http://www.foodforlovers.com/products, 3 pages.
Free & Easy Dairy Free Cheese Flavour Sauce Mix, Holland & Barrett, posted on or before Jun. 22, 2013, retrieved Feb. 7, 2014, http://www.hollandandbarrett.com/pages/product_detail.asp?pid = 2686, 2 pages.
Galaxy Foods Vegan Soy Grated Parmesan, ShopRite, retrieved Feb. 7, 2014, http://www.shoprite.com/pd/Galaxy-Nutritional-Foods/Vegan-Grated-Soy-Topping-Parmesan-Flavor/4-oz/077172640006/, 6 pages.
Go Veggie!, Dairy Free Products and Nutrition Facts, posted on or before 2013, accessed Feb. 7, 2014, http://goveggiefoods.com/our-products/dairy-free-cheese-alternative-products/, 13 pages.
Heritage Health Food Creamy Veeta Cheeze Sauce Mix, Vegan Essentials, posted on or before Aug. 13, 2013, retrieved Feb. 7, 2014, http://store.veganessentials.com/creamy-veeta-cheeze-sauce-mix-by-heritage-health-food-p3945.aspx, 1 page.
Leahy Gardens Vegan & Delicious, Macaroni & Cheese and Cheese Flavored Sauce Mix Product and Nutrition Facts, posted on or before Feb. 8, 2010, retrieved Feb. 7, 2014, http://www.leaheyfoods.com/products/MacCheese.aspx, 3 pages.
Lisanatti Foods, Vegan Cheeze Products and Nutrition Facts, posted on or before Mar. 26, 2013, retrieved Feb. 7, 2014, http://www.lisanatti.com/index.php?option=com_zoo&view=category&layout=category&Itemid=22, 5 pages.
Nacho Mom's Vegan Queso, Products and Nutrition Facts, posted on or before Sep. 20, 2010, retrieved on Feb. 7, 2014, http://fatgoblin.com/Home.html, 6 pages.
Nutty Cow Nut Cheeses, Products and Nutrition Facts, posted on or before Jul. 23, 2012, retrieved Feb. 7, 2014, http://www.nuttycow.com/, 6 pages.
Parmela Parmesan Style Aged Nut Cheese, Product and Nutrition Facts, 2012, retrieved Feb. 7, 2014, http://www.parmelafoods.com/your-health.html, 4 pages.
Peace Cheese 100% Plant-based Cheese Alternative, Product and Nutrition Facts, posted on or before Jun. 6, 2012, retrieved Feb. 7, 2014, http://www.ilovepeacecheese.com/#/products/457164262, 3 pages.
Punk Rawk Labs: an ongoing experiment in optimal health, Nut Milk Cheese Products, posted on or before Jun. 8, 2011, retrieved Feb. 7, 2014, http://www.punkrawklabs.net/cheeses.html, 4 pages.
Road's End Organics, Cheese Sauce Mix Products and Nutrition Facts, posted on or before Oct. 28, 2009, retrieved Feb. 7, 2014, http://www.edwardandsons.com/reo_shop_chreese.itml, 6 pages.
Road's End Organics, Mac & Chreese Products and Nutrition Facts, posted on or before Oct. 28, 2009, retrieved Feb. 7, 2014, http://www.edwardandsons.com/reo_shop_pastas.itml, 7 pages.
Sister River Foods Parma!, Products and Nutrition Facts, Posted on or before Jun. 2, 2012, retrieved Feb. 11, 2014, http://www.veganstore.com/product/parma-vegan-parmesan/vegan-cheese-and-diary-alternatives, 6 pages.
Soy Kaas, Products, posted on or before Jan. 20, 2011, retrieved Feb. 11, 2014, http://www.soykaas.com/products, 1 page.
Soyco Cheese Products, Natural Pantry, retrieved Feb. 11, 2014, http://www.natural-pantry.com/search_results.asp?et=All&site_search_qu=soyco&storeID=D92VLAQVMPDL9L5UHTS2WLU67NADEHUA, 10 pages.
Soymage Cheese Products, Good Earth Natural Foods, retrieved on Feb. 11, 2014, http://www.goodearthnaturalfoods.com/shop/brand2.asp?storeID=PJ102JRNHNGT8G0QMPEQ7LDC7GX6C2W2&alpha=S&brand=Soymage&brand_id=805, 6 pages.
Ste Martaen Cheese, Products and Nutrition Facts, posted on or before May 28, 2009, retrieved Feb. 11, 2014, http://stemartaen.bigcartel.com/, 14 pages.
The Daiya Advantage, Products and Nutrition Facts, posted on or before Jan. 26, 2010, retrieved on Feb. 7, 2014, http://us.daiyafoods.com/our-products, 126 pages.

The Vegetarian Express Parma Zaan Sprinkles, posted on or about Oct. 17, 2009, retrieved Feb. 11, 2014, http://www.thevegetarianexpress.com/cart/home.php?cat=250, 2 pages.
Tofu Rella Mozzarella Cheese, Natural Pantry, retrieved Feb. 11, 2014, http://www.natural-pantry.com/shop/product_view.asp?id = 24684&StoreID=D92VLAQVMPDL9L5UHTS2WLU67NADEHUA&private_product=0, 2 pages.
Tofutti Cheese Products and Nutrition, posted on or before Jun. 26, 2013, retrieved Feb. 11, 2014, http://www.tofutti.com/dairy-free-cheeses/, 18 pages.
Trader Joe's Sliced Soy Cheese Alternative, Fotki, posted Oct. 27, 2008, retrieved Feb. 11, 2014, http://public.fotki.com/harwons/food/tj-sliced-soy-cheese.html., 1 pages.
Trader Joe's Vegan Mozzarella, A(soy) Bean, posted Jun. 7, 2013, retrieved Feb. 11, 2014, http://a-soy-bean.blogspot.com/2013/06/showdown-trader-joes-vegan-mozzarella.html, 13 pages.
Treeline Treenut Cheese, Products and Nutrition Facts, posted on or before Dec. 10, 2013, retrieved on Feb. 11, 2014, http://www.treelinecheese.com/treeline-cheese-products.html, 3 pages.
Vegan Sun Artisan Aged Raw Cheese, Vegan Essentials, retrieved Feb. 11, 2014, http://store.veganessentials.com/vegan-sun-artisan-aged-raw-cheese-p4201.aspx, 3 pages.
VegCuisine Soy Cheese Products, The Vegan Store, retrieved on Feb. 11, 2014, http://www.veganstore.com/category/s?keyword=vegcuisine, 5 pages.
Veggie Brothers Mozzarella Sticks, Vegan Essentials, Nov. 9, 2013, retrieved Feb. 11, 2014, http://store.veganessentials.com/vegan-mozzarella-sticks-by-veggie-brothers-p3761.aspx, 2 pages.
Victoria Vegan Sauces, Products and Nutrition Facts, posted on or about Sep. 16, 2012, retrieved Feb. 11, 2014, http://www.victoriafinefoods.com/products/specialty-sauces/victoria-vegan, 9 pages.
Wayfare We Can't say It's Cheese Spread, Products and Nutrition Facts, posted on or about Oct. 12, 2013, retrieved Feb. 11, 2014, http://www.wayfarefoods.com/we-cant-say-its-cheese/, 5 pages.
Welcome to VBites Foods, Cheezly Products and Nutrition Facts, 2013, retrieved on Feb. 7, 2014, http://www.vbitesfoods.com/meat-free/cheezly.html, 26 pages.
Yves Veggie Cuisine The Good Slice, ShopWell, retrieved on Feb. 11, 2014, http://www.shop-well.com/yves-vegeie-cuisine-the-good-slice-cheese-altentative-cheddar-style/soy-foods/p/6082260001, 1 page.
"Acidified Milk Products and Protein Stabilisation," Herbstreith & Fox, retrieved on Mar. 3, 2014, http://www.herbstreith-fox.de/en/informative-literature/informative-literature-from-rd-and-tech-application.html, 15 pages.
"Ice Cream and Ice Cream Desserts," Herbstreith & Fox, retrieved on Mar. 3, 2014, http://www.herbstreith-fox.de/en/informative-literature/informative-literature-from-rd-and-tech-application.html, 5 pages.
"Innovation at Its Best: 5 Years of Food Valley Awards," Food Valley, retrieved on Mar. 7, 2014, http://www.foodvalley.nl/English/Afbeeldingen/FVAjubileumuitgave/Innovation%20at%20Its%20Best%20-%205%20Years%20of%20Food%20Valley%20Awards.pdf, 51 pages.
"Low Methylester Amidated Pectins," Herbstreith & Fox, retrieved on Mar. 3, 2014, http://www.herbstreith-fox.de/en/informative-literature/informative-literature-from-rd-and-tech-application.html, 13 pages.
"Stabilisation of Whey and Whey Mix Products with Pectin," Herbstreith & Fox, retrieved on Mar. 3, 2014, http://www.herbstreith-fox.de/en/informative-literature-informative-literature-from-rd-and-tech-application.html, 6 Pages.
"Texturising of Fermented Milk Products," Herbstreith & Fox, retrieved on Mar. 3, 2014, http://www.herbstreith-fox.de/en/informative-literature/informative-literature-from-rd-and-tech-application.html, 6 pages.
Kanani, "The Future of Meat is Meatless, Just as Tasty, and About to Change the World," Forbes, Mar. 6, 2014, retrieved on Mar. 18, 2014,

(56) References Cited

OTHER PUBLICATIONS http://www.forbes.com/sites/rahimkanani/2014/03/06/the-future-of-meat-is-meatless-just-as-tasty-and-about-to-change-the-world/, 13 pages.
Connelly and Piper, "Person of the Year: Tal Ronnen," *VegNews*, Nov./Dec. 2013, 29-32.
Duane, "Engineering the Future of Artisanal Vegan Cheese," *Food & Wine*, Nov. 2013, http://www.foodandwine.com/articles/engineering-the-future-of-artisanal-vegan-cheese, 5 pages.
Hanlon, "Fake Meat: is science fiction on the verge of becoming fact?," The Guardian, Jun. 22, 2012, http://www.theguardian.com/science/2012/jun/22/fake-meat-scientific-breakthroughs-research, 7 pages.
Herper, "Drop that Burger," *Forbes Online*, Nov. 12, 2009, http://www.forbes.com.forbes/2009/1130/thought-leaders-mcdonalds-global-warming-drop.that-burger.html, 4 pages.
Schwartz, "Meet the Silicon Valley-Backed Cheese That You Might Actually Eat," Fast Company, Feb. 26, 2014, retrieved May 19, 2014, http://www.fastcoexist.com/3025648/meet-the-silicon-valley-backed-vegan-cheese-that-you-might-actually-eat, 3 pages.
Wortham and Miller, "Venture Capitalists York Times Bigger Bets on Food Start-Ups," The New York Times Online, Apr. 28, 2013, http://www.nytimes.com/2013/04/29/business/venture-capitalists-are-making-bigger-bets-on-food-start-ups.html?pagewanted=all&_r=1&, 4 pages.
Davis et al., "Some Rheological Properties of Aqueous Peanut Flour Dipersions," J. Texture Studies, 2007, 38:253-272.
Ellis et al., "Structure of ferric soybean leghemoglobin a nicotinate at 2.3 A resolution," Acta Crystallographica, May 1997, Section D, 53(3):302-310.
Gharst, "Biochemical and Rheological Characteristics of Peanut Proteins Crosslinked with Microbial Transglutaminase," A dissertation submitted to the Graduate Faculty of North Carolina State University, Raleigh NC, 2007, 149 pages.
Gharst, "The Effect of Transglutaminase Crosslinking on the Rheological Characteristics of Heated Peanut Flour Dispersions," J. Food Sci., 2007, 72(7):C369-C375.
Gharst, "Effects of Transglutaminase Catalysis on the Functional and Immunoglobulin Binding Properties of Peanut Flour Dispersions Containing Casein," J. Agric. Food Chem., 2008, 56:10913-10921.

\* cited by examiner

METHODS AND COMPOSITIONS FOR CONSUMABLES

CROSS-REFERENCE TO RELATED APPLICATIONS

This application is a continuation of PCT/US2012/046552, filed Jul. 12, 2012, which claims priority to U.S. Application Ser. No. 61/507,096, filed Jul. 12, 2011, the disclosures of which are incorporated herein by reference in their entirety.

BACKGROUND OF THE INVENTION

Cheese making has relied on dairy milks as the major ingredient for more than 4000 years. Dairy cheese is made from curds formed from dairy milk. Dairy milks can readily be made to form curds suitable for making cheese by contacting the dairy milk with rennet (an aspartic protease which cleaves kappa-casein) at mildly acidic pH. Some cheeses, e.g., cream cheese, ricotta, cottage cheese and paneer, are made without rennet. In the absence of rennet, dairy cheese may be induced to curdle with acid (e.g., lemon juice, vinegar, etc.) or a combination of heat and acid. Acid coagulation can also occur naturally from starter culture fermentation. The strength of the curds depends on the type of coagulation. Most commercially produced cheeses use some type of rennet (animal, vegetable or microbial-derived) in their production.

The global dairy sector contributes an estimated 4 percent to the total global anthropogenic green house gas emissions. Producing 1 kg of cheddar cheese requires an average of 10,000 Liters of fresh water. Additionally, many individuals cannot digest and metabolize lactose. In these individuals enteric bacteria ferment the lactose, resulting in various abdominal symptoms, which can include abdominal pain, bloating, flatulence, diarrhea, nausea, and acid reflux. Additionally, the presence of lactose and its fermentation products raises the osmotic pressure of the colon contents. 3.4% of children in the U.S.A. are reported to have allergies to dairy milks. Many individuals choose to avoid milk for ethical or religious reasons.

Non-dairy milks, including plant-derived milks avoid many of the environmental, food sensitivity, ethical and religious problems associated with dairy milk and they can be made free of lactose, making the generation of dairy substitutes using the plant derived milks attractive. However, rennet is not an effective agent for inducing non-dairy proteins or emulsions, including plant-derived milks, including almond milk, chestnut milk, pecan milk, hazelnut milk, cashew milk, pine nut milk, and walnut milk, to curdle. Consequently, traditional cheese making techniques have not been successfully used to produce non-dairy cheese replicas.

Flavor and aroma in dairy cheese results in part from the degradation of lactose, proteins and fats, carried out by ripening agents, which include: bacteria and enzymes in the milk, bacterial cultures added during the cheese-making process, rennet, other proteases, lipases, added molds and/or yeasts and bacteria and fungi that opportunistically colonize the cheese during ripening and aging.

Cheese replicas made principally of non-dairy ingredients are commercially available. Most of these cheese replicas include some dairy ingredients, for example, casein. Some commercially available cheese replicas contain no animal products. These include fermented cheese replicas made from nut milks from which insoluble carbohydrates have not been effectively removed, and made without using a protein crosslinking agent and several products in which a starch is a principal ingredient or containing agar, carrageenan and tofu to provide the desired texture. Most tasters consider none of the currently available cheese replicas to adequately replicate the taste, aroma and mouthfeel of dairy cheeses.

Complex carbohydrates in currently available cheese replicas made from nut milks have unfavorable effects on the texture, resulting in a product with a grainy mouthfeel and lacking the creaminess of dairy cheeses.

Starches that comprise the major gelling agent in many currently available cheese replicas lead to a relatively high carbohydrate content, which may be undesirable to consumers, for example those wishing to limit carbohydrate intake.

Because of these deficiencies, there is currently no cheese replica that is acceptable to most consumers as an alternative to traditional dairy cheeses.

Thus, it is clear that there is a great need in the art for an improved method and system for producing non-dairy cheese replicas while avoiding the shortcomings and drawbacks of the cheese replicas that have previously been available to consumers.

SUMMARY OF THE INVENTION

The invention relates to methods and compositions for non-dairy milk and cheese products, including without limitation, plant-derived milk and cheese products, as an alternative to dairy products for human consumption.

The invention provides a method for producing a non-dairy cheese by preparing an emulsion comprising proteins and fats from plants or other non-animal sources, inducing the emulsion to form a gel by enzymatic cross-linking of the proteins or denaturing the proteins, and producing a cheese-replica from the gel. In one embodiment, the emulsion contains less than 10% animal products. In one embodiment, the emulsion contains less than 8%, 7%, 6%, 5%, or 3% animal products. In one embodiment the emulsion contains no animal products. In one embodiment the inducing step of said method comprises adding an enzyme. In one embodiment of said method the enzyme used is transglutaminase. In one embodiment the enzyme used is Factor XIII (fibrin-stabilizing factor). In one embodiment of said method the enzyme used is Keratinocyte transglutaminase (TGM1). In one embodiment the enzyme used is Tissue transglutaminase (TGM2). In one embodiment of said method the enzyme used is Epidermal transglutaminase (TGM3). In one embodiment the enzyme used is Prostate transglutaminase (TGM4). In one embodiment the enzyme used is TGM X (TGM5). In one embodiment of said method the enzyme used is TGM Y (TGM6). In one embodiment of said method the enzyme used is TGM Z (TGM7). In one embodiment, the enzyme is a transglutaminase from *Streptoverticillium mobaraense*. In one embodiment, the enzyme is similar or identical to a transglutaminase from *Streptoverticillium mobaraense*. In one embodiment, the enzyme is a lysyl oxidase. In one embodiment the emulsion is non-dairy milk. In one embodiment at least one of the plant sources are nuts. In one embodiment at least one of the plant sources are legumes. In one embodiment at least one of the plant sources are seeds. In one embodiment at least one of the plant sources are leaves. In one embodiment at least one of the plant sources are fruit from the family Fabaceae. In one embodiment at least one of the non-animal sources is a species of bacteria. In one embodiment at least one of the non-animal sources is a species of archaea. In one embodiment at least one of the non-animal sources is a species of fungus. In one embodiment at least one of the non-animal sources is a species of algae. In one embodiment the emulsion is a non-dairy milk. In one embodiment the nuts are one or more of following: almonds, cashews, brazilnuts, chestnuts, coconuts, hazelnuts, macadamia nuts, peanuts, pecans, pistachios or walnuts. One embodiment of said method has an additional step of adding a sugar to the emulsion. In one embodiment the sugar added to the emulsion is a monosaccharide. In one embodiment the sugar added to the emulsion is a disaccharide. In one embodiment said method has an additional step of inoculating with lactic acid bacteria. In the embodiment of inoculating with lactic acid bacteria the invention provides an addition step of allowing growth of the bacterial cultures. In one embodiment the method can include an additional step of adding one or more of the following *Penicillium camemberti, Geotrichum candidum, Penicilliem roqueforti, Penicillium nalgiovensis, Verticillium lecanii, Kluyveromyces lactis, Saccharomyces cerevisiae, Candida utilis, Debaryomyces hansensil, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., or *Propionibacteria*. In one embodiment the method can include an additional step of adding one or more of the following *halophilc* bacterium or *archaea*. In one embodiment the invention provides for the use of thermal denaturing and cross-linking. In one embodiment the invention provides thermal denaturing used without the addition of any enzymes. One embodiment of said method has an additional step of cutting the gel. One embodiment of said method has an additional step of draining and shaping the cut gel. One embodiment of said method has an additional step of adding a flavoring component. In one embodiment the flavoring component is one or more species of bacteria. In one embodiment the flavoring component is lactic acid bacteria. In one embodiment the flavoring component is a mold. In one embodiment the flavoring component is yeast. In one embodiment the method includes concentrated proteins prior to preparing the emulsion. In one embodiment the concentrated proteins are each essentially homogeneous proteins. In one embodiment the method includes the additional step of concentrating proteins and fats from one or more plant sources. In one embodiment the method includes the additional step of concentrating proteins and fats from one or more non-animal sources. In one embodiment the method includes the additional step of isolating the proteins and fats from one or more plant sources. In one embodiment the method includes the additional step of isolating the proteins and fats from one or more non-animal sources. In one embodiment the method includes the additional step of purifying the proteins and fats from one or more plant sources. In one embodiment the method includes the additional step of purifying the proteins and fats from one or more non-animal sources. In one embodiment the invention provides for the concentrated proteins to come from the same essentially homogeneous plant-derived protein. In one embodiment the invention provides for the concentrated proteins to come from the same essentially homogeneous non-animal-derived protein. In one embodiment the invention provides for the concentrated proteins to come from separate plant species. In one embodiment the invention provides for the concentrated proteins to come from separate non-animal species.

In addition, the invention provides steps for preparation to undertake the claimed methods of producing a non-animal based cheese including (a) obtaining nuts or seeds, and (b) surface sterilizing the nuts or seeds. In one embodiment the method uses nuts or seeds as the plant sources. In one embodiment the surface sterilization step is blanching procedure. In one embodiment the preparation method can also include a step for washing the nuts or seeds. In one embodiment the method of preparation can also include the step of decompounding the nuts or seeds. In one embodiment the step of decompounding the nuts or seeds is a blending procedure. In one embodiment the method of preparation can also include centrifugation. In one embodiment the method of preparation can also includes a centrifugation procedure that results in the removal of at least 85% of the suspended solids. In one embodiment the method of preparation can also includes a centrifugation procedure that results in the removal of at least 75%, 65%, 55%, or 45% of the suspended solids.

The invention provides a method comprising decompounding nuts or seeds in water, removing at least 85% of the suspended solids and adding a transglutaminase to catalyze the formation of crosslinks between proteins from the nuts or seeds.

The invention provides a method for making a non-dairy cheese replica comprising, obtaining nut milk, centrifugation of the nut milk to remove insoluble matter, and crosslinking proteins within the nut milk with transglutaminase.

In one embodiment the invention provides a composition comprising centrifuged non-dairy milk wherein at least 85% of the insoluble solids have been removed relative to the non-dairy milk prior to centrifugation.

In one embodiment the invention provides a composition comprising a non-dairy milk with less than 30% polysaccharides. In one embodiment the non-dairy milk composition has less than 10% polysaccharides. In one embodiment the non-dairy milk composition less than 1% polysaccharides. In one embodiment the non-dairy milk composition is entirely composed of ingredients derived from non-animal sources. In one embodiment the non-dairy milk composition is at least comprised of 20% protein isolated from a single plant species.

In one embodiment the invention provides for a composition comprised of non-dairy milk and a cross-linking enzyme. In one embodiment of the non-dairy milk and a cross-linking enzyme composition the cross-linking enzyme is Factor XIII (fibrin-stabilizing factor). In one embodiment of the non-dairy milk and a cross-linking enzyme composition, the enzyme is a transglutaminase from *Streptoverticillium mobaraense*. In one embodiment of the non-dairy milk and a cross-linking enzyme composition, the enzyme is similar or identical to a transglutaminase from *Streptoverticillium mobaraense*. In one embodiment of the non-dairy milk and a cross-linking enzyme composition the cross-linking enzyme is Keratinocyte transglutaminase (TGM1). In one embodiment of the non-dairy milk and a cross-linking enzyme composition the cross-linking enzyme is Tissue transglutaminase (TGM2). In one embodiment of the non-dairy milk and a cross-linking enzyme composition the cross-linking enzyme is Epidermal transglutaminase (TGM3). In one embodiment of the non-dairy milk and a cross-linking enzyme composition the cross-linking enzyme is Prostate transglutaminase (TGM4). In one embodiment of the non-dairy milk and a cross-linking enzyme composition the cross-linking enzyme is TGM X (TGM5). In one embodiment of the non-dairy milk and a cross-linking enzyme composition the cross-linking enzyme is TGM Y (TGM6). In one embodiment of the non-dairy milk and a cross-linking enzyme composition the cross-linking enzyme is TGM Z (TGM7). In one embodiment the invention provides for a composition comprised of non-dairy milk and a cross-linking enzyme. In one embodiment of the non-dairy milk and a cross-linking enzyme composition the cross-linking enzyme is lysyl oxidase. In one embodiment of the composition comprising non-dairy milk and a cross-linking enzyme, protein crosslinks are formed between glutamine and lysine side chains of respective protein constituents.

In one embodiment of the non-dairy milk and a cross-linking enzyme composition, at least 85% of the insoluble solids have been removed by centrifugation. In one embodiment of the non-dairy milk and a cross-linking enzyme composition, proteins from non-animal sources comprise at least 50% of the total mass of the composition. In one embodiment of the non-dairy milk and a cross-linking enzyme composition the starch content is less than 1% by mass. In one embodiment of the non-dairy milk and a cross-linking enzyme composition is the starch content is less than 5% by mass. One embodiment of the non-dairy milk and a cross-linking enzyme composition has less than 1% insoluble carbohydrate by mass. One embodiment the non-dairy milk and a cross-linking enzyme composition has less than 5% insoluble carbohydrate by mass. One embodiment the non-dairy milk and a cross-linking enzyme composition has less than 5% starch and less than 1% insoluble carbohydrate by mass. One embodiment the non-dairy milk and a cross-linking enzyme composition has less than 5% starch and less than 5% insoluble carbohydrate by mass. In one embodiment the non-dairy milk and a cross-linking enzyme composition has a polysaccharide content less than 1% by mass. In one embodiment the non-dairy milk and a cross-linking enzyme composition has a polysaccharide content less than 5% by mass. In one embodiment the non-dairy milk and a cross-linking enzyme composition has a carbohydrate content less than 1% by mass. In one embodiment the non-dairy milk and a cross-linking enzyme composition has a carbohydrate content less than 5% by mass. In one embodiment the non-dairy milk and a cross-linking enzyme composition has a carbohydrate content less than 10% by mass. In one embodiment of the non-dairy milk and a cross-linking enzyme composition, at least 80% of the protein content comprises a single monomeric or multimeric protein.

In some embodiments the invention provides for a composition comprising covalently crosslinked non-dairy proteins, a crosslinking enzyme, and cheese microbes. In one embodiment of the composition of covalently crosslinked non-dairy proteins, a crosslinking enzyme, and cheese microbes composition, the proteins are not from soy. In one embodiment of the composition comprising covalently crosslinked non-dairy proteins, a crosslinking enzyme, and cheese microbes, less than 5% of the proteins are from soy. In one embodiment the composition comprises less than 20% insoluble solids. In one embodiment the covalently crosslinked non-dairy proteins, a crosslinking enzyme, and cheese microbes composition also contains oils or fats isolated from non-dairy sources. In one embodiment of the composition comprising covalently crosslinked non-dairy proteins, a crosslinking enzyme, and cheese microbes the crosslinking enzyme of the composition is a transglutaminase. In one embodiment of the composition comprising covalently crosslinked non-dairy proteins, a crosslinking enzyme, and cheese microbes the crosslinking enzyme of the composition is a lysyl oxidase. In one embodiment of the composition comprising covalently crosslinked non-dairy proteins, a crosslinking enzyme, and cheese microbes the cross-linking enzyme is Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), TGM Z (TGM7. In one embodiment of the composition comprising non-dairy milk and a cross-linking enzyme and cheese microbes, the enzyme is a transglutaminase from *Streptoverticillium mobaraense*. In one embodiment of the composition comprising non-dairy milk and a cross-linking enzyme and cheese microbes, the enzyme is similar or identical to a transglutaminase from *Streptoverticillium mobaraense*. In one embodiment of the composition comprising non-dairy milk and a cross-linking enzyme and cheese microbes, protein crosslinks are formed between glutamine and lysine side chains of respective protein constituents. In one embodiment of the composition comprising non-dairy milk and a cross-linking enzyme and cheese microbes, protein crosslinks are formed between lysine side chains of respective protein constituents.

In some embodiments the invention provides for a cheese replica composition comprised of a gelled emulsion of non-dairy proteins and fats. In one embodiment the cheese replica composition has between 10% and 40% proteins from non-dairy sources and between 0% and 65% fats from non-dairy sources. In one embodiment the cheese replica composition further comprises a crosslinking enzyme selected from the group consisting of Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6) or TGM Z (TGM7). In one embodiment of the cheese replica composition, the enzyme is a transglutaminase from *Streptoverticillium mobaraense*. In one embodiment of the cheese replica composition, the enzyme is similar or identical to a transglutaminase from *Streptoverticillium mobaraense*. In one embodiment of the cheese replica composition, protein crosslinks are formed between glutamine and lysine side chains of respective protein constituents. In one embodiment of the cheese replica composition, protein crosslinks are formed between lysine side chains of respective protein constituents. In some embodiment of the cheese replica composition, formation of protein crosslinks is catalyzed by a lysyl oxidase.

In one embodiment the cheese replica composition further comprises cheese-making microbes. In one embodiment the cheese replica composition has one or more cheese-making microbes from the group consisting of *Penicillium camemberti, Geotrichum candidum, Penicilliem roqueforti, Penicillium nalgiovensis, Verticillium lecanii, Kluyveromyces lactis, Saccharomyces cerevisiae, Candida utilis, Debaryomyces hansensil, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., or *Propionibacteria*.

In some embodiments the invention provides for a cheese replica composition, wherein the cheese replica is a cheese equivalent according to a human. In some embodiments the invention provides for a cheese replica composition, wherein human subjects cannot distinguish the cheese replica from a dairy cheese. In one embodiment of the cheese replica at least 20% of the protein content comprises a single monomeric or multimeric protein. In one embodiment the cheese replica composition is made without the addition of starches or rennet or any other extrinsic proteases other than those contributed by microbial cultures. In one embodiment the cheese replica composition has a pH less than 5.5 where the acidification was accomplished solely by microbial fermentation. In one embodiment the cheese replica composition has a pH less than 5 where the acidification was accomplished solely by microbial fermentation. In one embodiment the cheese replica composition has a pH less than 6 where the acidification was accomplished solely by microbial. In one embodiment the cheese replica composition is contains no animal products. In one embodiment the cheese replica has less than 5% by mass insoluble carbohydrates. In one embodiment the cheese replica composition contains no rennet, vinegar, or lemon juice.

In some embodiments the invention provides for a cheese replica composition made with the addition of rennet or any aspartic protease or any other type protease (e.g., serine protease) to affect or enhance the flavor and/or aroma and/or texture of the cheese replica.

In some embodiments the invention provides for a cheese replica composition made with the addition of vinegar, lemon juice or any other type of acid to affect or enhance the flavor and/or aroma and/or texture of the cheese replica.

In some embodiments the invention provides for a soft fresh cheese replica composition composed of pasteurized almond milk, pasteurized macadamia nut milk, mesophilic starter culture, transglutaminase, water, and salt. In one embodiment the soft fresh cheese replica composition includes the addition of vinegar. In one embodiment the soft fresh cheese replica composition includes the addition of microbial coagulant. In one embodiment the soft fresh cheese replica composition includes the addition of vinegar and microbial coagulant.

In some embodiments the invention provides for a salted cheese replica composition composed of pasteurized almond milk, pasteurized macadamia nut milk, mesophilic starter culture, transglutaminase, and water. In one embodiment the salted cheese replica composition includes the addition of vinegar. In one embodiment the salted cheese replica composition includes a microbial coagulant. In one embodiment the salted cheese replica composition includes vinegar and a microbial coagulant.

In some embodiments the invention provides for a soft ripened cheese replica composition composed of pasteurized almond milk, pasteurized macadamia nut milk, mesophilic starter culture, flora danica, *Geotrichum candidum, Penicillium candidum, Debaromyces hansenii,* transglutaminase, water, and salt. In one embodiment the soft ripened cheese replica composition includes vinegar. In one embodiment the soft ripened cheese replica composition includes a microbial coagulant. In one embodiment the soft ripened cheese replica composition includes vinegar and microbial coagulant.

In some embodiments the invention provides for a goat cheese replica composition composed of pasteurized almond milk, macadamia nut milk, mesophilic starter culture, transglutaminase, water, and salt. In one embodiment the goat cheese replica composition includes vinegar. In one embodiment the goat cheese replica composition includes a microbial coagulant. In one embodiment the goat cheese replica composition includes vinegar and a microbial coagulant.

In some embodiments the invention provides a method for making a cheese replica comprising removing from a non-dairy milk a proportion of insoluble solids. In some embodiments the invention provides a method for making a cheese replica comprising removing from a plant-based milk a proportion of insoluble solids. In some embodiments the invention provides a method comprising centrifuging a non-dairy milk to sediment a proportion of insoluble solids. In some embodiments about 10%, about 20%, about 30%, about 40%, about 50%, about 60%, about 70%, about 80%, about 90%, or about 100% of the insoluble solids are removed.

In some embodiments the isolated or enriched proteins of the methods and compositions of the invention comprise one or more of: ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, glyceraldehyde-3-phosphate dehydrogenases, pyruvate decarboxylases, actins, translation elongation factors, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, zein, any seed storage protein, oleosins, caloleosins, steroleosins or other oil body proteins, vegetative storage protein A, vegetative storage protein B, moong seed storage 8S globulin.

In some embodiments the invention provides a composition comprising (A) covalently crosslinked plant-derived proteins from a set comprising ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, glyceraldehyde-3-phosphate dehydrogenases, pyruvate decarboxylases, actins, translation elongation factors, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, zein, any seed storage protein, oleosins, caloleosins, steroleosins or other oil body proteins, vegetative storage protein A, vegetative storage protein B, and moong seed storage 8S globulin; (B) a crosslinking enzyme, and (C) cheese microbes.

In some embodiments the invention provides a composition comprising (A) covalently crosslinked plant-derived proteins from a set comprising ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, glyceraldehyde-3-phosphate dehydrogenases, pyruvate decarboxylases, actins, translation elongation factors, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, zein, any seed storage protein, oleosins, caloleosins, steroleosins or other oil body proteins, vegetative storage protein A, vegetative storage protein B, and moong seed storage 8S globulin.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
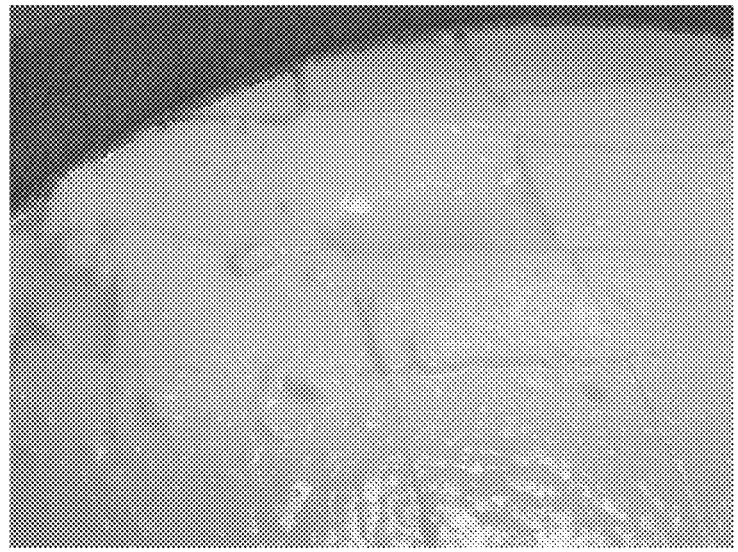
FIG. 1 shows freshly cut curds prepared by the method used to produce the soft fresh cheese replicas and salted cheese replicas described in the examples.

The present invention discloses methods and compositions based upon the realization that transglutaminase efficiently crosslinks the proteins in many non-dairy milks to produce a soft, moist, elastic gel (a "curdling" of non-dairy milks). This process allows the separation of the crosslinked proteins and associated fats from the "whey." The crosslinked proteins can hold a fat emulsion, and have the essential physical characteristics needed for pressing, culturing and ripening a cheese replica derived from non-dairy milk. In various embodiments the current invention includes cheese replicas principally, entirely or partially composed of ingredients derived from non-animal sources. In additional embodiments the present invention includes methods for making cheese replicas from non-animal sources. In various embodiments these results are achieved by replicating the curdling process of cheese making in non-dairy milks using enzymes.

The term a cheese "substitute" or "replica" can be any non-dairy product that serves a role as food or in food that is commonly served by traditional dairy cheese. A cheese "substitute" or "replica" can be a product that shares visual, olfactory, textural or taste characteristics of cheese such that an ordinary human observer of the product is induced to think of traditional dairy cheese.

A purified protein can be a preparation in which the cumulative abundance by mass of protein components other than the specified protein, which can be a single monomeric or multimeric protein species, is reduced by a factor of 3 or more, or a factor of 5 or more, or a factor of 10 or more relative to the source material from which the specified protein was said to be purified.

The term "homogeneous" can mean a single protein component comprises more than 90% by mass of the total protein constituents of a preparation.

The term resemble can mean one composition having characteristics recognizably similar to another composition by an ordinary human observer.

The term "indistinguishable" can mean that an ordinary human observer would not be able to differentiate two compositions based on one or more characteristics. It is possible that two compositions are indistinguishable based on one characteristic but not based on another, for example two compositions can have indistinguishable taste while having colors that are different. Indistinguishable can also mean that the product provides an equivalent function as or performs an equivalent role as the product for which it is substituting.

I. Non-Dairy Milks

Cheese replicas may be made using non-dairy milk prepared from nuts or plant seeds. For example almonds, cashews, brazilnuts, chestnuts, coconuts, hazelnuts, macadamia nuts, peanuts, pecans, pistachios or walnuts can provide non-dairy milk that, in various embodiments of the invention, is used to produce cheese replicas. Nuts can include so called "true nuts" as well as a wide variety of dried seeds from of plants. Any large, oily kernel found within a shell and used in food may be regarded as a nut. Plant seeds can include a wide variety embryonic plants enclosed in a seed coat. Plant seeds can include for example legumes, cereals, and gymnosperms. Non-dairy products or compositions include products or compositions where the constituent proteins, fats and/or small molecules can be isolated from or secreted by plants, bacteria, viruses, archaea, fungi, algae, or they can be made synthetically by chemical synthesis or in vitro. Non-dairy products are generally not derived from cows, goats, buffalo, sheep, horses, camels, or other mammals. In some embodiments non-dairy products do not contain dairy proteins. In some embodiments non-dairy products do not contain dairy fats. In some embodiments non-dairy products do not contain enzymes derived from an animal.

The nuts or seeds of the present invention can be raw. In some embodiments the nuts or seeds used to produce non-dairy milk are all raw. Alternatively some or all of the nuts or seeds used in the production of a non-dairy milk can be processed. The processed nuts or seed can be roasted, dry roasted, toasted, or baked.

Milk, or non-dairy milk, can mean an emulsion comprising proteins and fats or a solution or suspension of proteins, sometimes further comprising other solutes that might include carbohydrates, salts and other small molecules that contribute to flavor, texture, emulsion stability, protein solubility or suspension stability, or its ability to support growth of microbial cultures used in making cheese replicas, yogurt replicas, or other replicas of cultured dairy products.

The non-dairy milk can be made by a method comprising preparing the nuts or plant seeds with processing steps such as sterilizing, blanching, shocking, decompounding, centrifugation, or washing.

The non-dairy milks can be produced by decompounding the nuts or plant seeds, for example by grinding or blending or milling the nuts in a solution comprising water. In various embodiments alternative methods for decompounding the nuts or dried seeds include crushing, tumbling, crumbling, atomizing, shaving, pulverizing, grinding, milling, water eroding (for example with a water jet), or finely chopping the nuts or plant seeds. In some embodiments the decompounding step takes place in a blender. In some embodiments the decompounding is in a continuous flow grinder. In some embodiments the decompounding is in a continuous flow mill. The decompounding can be followed by a sorting, filtering, screening, or separation step. In some embodiments the decompounded nuts or seeds can be stored prior to the formation of a non-dairy milk. In some embodiments an aqueous solution is added before, during, or after the decompounding.

The nuts or seeds used in some embodiments of the invention to make non-dairy milks may have contaminants on the surface which would make a non-dairy milk unsafe or unpalatable. Accordingly the nuts or seeds can be washed prior to use. The nuts or seeds can also be sterilized to remove, reduce, or kill any contaminants on the surface of the nuts or seeds. A sterilization step can be an irradiation step, a heat step (e.g. steam sterilization, flaming, or dry heat), or a chemical sterilization (e.g, exposure to ozone). In some embodiments the sterilization step kills more than 95% of microbes on the nuts or seeds. In some embodiments the sterilization step kills more than 99% of microbes on the nuts or seeds. Blanching is a process wherein the food is exposed to hot water (e.g. boiling), removed after a brief timed interval, and finally cooled by exposure to cold water (e.g. iced or cold running water). When nuts, such as almonds or pistachios, are blanched, the skin of the nut (botanically the seed coat surrounding the embryo) softens and can be easily removed later. Accordingly, in some embodiments the invention provides for non-dairy milk compositions with a reduced percentage of components found in the skin of the nut or seed. For example the composition can have 50%, 40%, 30%, 20%, 10% or less than 5% of the seed coat remaining after the preparation process. In some embodiments the invention provides for methods for making a non-dairy milk comprising removing the seed coat.

In one embodiment the blanching procedure is as follows: Place nuts into 212° F. heated water and blanch for 30 seconds. Drain nuts. Immediately move drained nuts into cold water. In some embodiments the temperature of the water is altered by 5%, 10% or 20%. In some embodiments the cold water temperature is about 0° C., 5° C., 10° C., or 20° C. In some embodiments the blanching takes about 10, 20, 30, 40, 50 seconds or about 1, 2, or 5 minutes.

In some embodiments the nuts or seeds can be hydrated, for example by immersion in water for 1, 2, 3, 4, 5, 6, 7, 8, 9, 10, 11, 12, 13, 14, 15, 16, 17, 18, 19, 20, 21, 22, 23, or 24 hours. In some embodiments the hydration step lasts multiple days. In some embodiments the water contains other components such as salts or preservatives. In some embodiments the water is maintained at a constant cool temperature. In some embodiments the hydration step can occur prior to the decompounding step.

In some embodiments the nuts or seeds can be dried, for example by exposure to a low humidity and/or heated environment for 1, 2, 3, 4, 5, 6, 7, 8, 9, 10, 11, 12, 13, 14, 15, 16, 17, 18, 19, 20, 21, 22, 23, or 24 hours. In some embodiments the drying step lasts multiple days. The drying step can occur prior to the decompounding step or the drying step can occur after a decompounding step.

In one embodiment the decompounding step is a blending procedure as follows: Place nuts in a clean and sanitized blender. Add clean fresh water to the blender. Turn on the blender and gradually increase speed up to maximum, blending for 5 minutes. Accumulate blended slurry in clean and sanitized ice cold container. Immediately begin rapid cooling of slurry by stirring slurry. Once the slurry has cooled to 50° F., move slurry to refrigerator to continue cooling to below 41° F. Allow slurry to rest at 36° F. overnight or up to 12 hours at 36° F. In some embodiments the blending times and speeds are altered by up to 100%. In some embodiments the temperatures are altered up to 20°.

Insoluble solids may be present in milks prepared by decompounding (e.g. grinding or blending) nuts or seeds. One surprising observation of the present invention is that these insoluble materials can hinder the formation of curds from the non-dairy milks. Insoluble solids can also result in curds or cheese replicas having a texture or mouthfeel perceived as grainy or pasty in comparison to the smoother, creamier texture of dairy cheese. Accordingly provided herein are methods for removing these insoluble materials and compositions of non-dairy milks and cheese replicas with reduced amounts of the insoluble materials. Compositions of the invention can have a mouthfeel or texture indicative of the absence of insoluble solids. For example a cheese replica can have a mouthfeel indicative of the absence of insoluble solids. The insoluble materials can comprise carbohydrates.

In some embodiments the methods for producing cheese replicas includes a step for the removal of solids from non-dairy milks prior to curdling. For example, in some embodiments, the non-dairy milks are centrifuged to remove the insoluble solids. In some embodiments the present invention provides for a non-dairy cheese replica with less than 1%, 5%, 10%, 20%, 30%, 40% or 50% of insoluble solids found in the non-dairy milk before removal of the insoluble solids. In some embodiments the present invention provides for a non-dairy milk extract with less than 1%, 5%, 10%, 20%, 30%, 40% or 50% of insoluble solids found in non-dairy milk. In some embodiments the present invention provides for a non-dairy milk with 99%, 95%, 90%, 80%, 70%, 60% or 50% of insoluble solids found in non-dairy milk removed.

In one embodiment the centrifugation procedure is as follows: Pour decompounded nut or seed slurry into container. Using a centrifuge with the JS-5.0 rotor, spin at about 5000 RPM for 30 mins. In some embodiments the spin is at about 500, 1000, 1500, 2000, 2500, 3000, 3500, 4000, 4500, 5000, 5500, 6000, 6500, 7000, 7500, 8000, 8500, 9000, 9500, or 10,000 RPM for about 5, 10, 15, 20, 25, 30, 35, 40, 45, 50, 55, or 60 minutes. In some embodiments the centrifugation speed or time is altered, for example by 20%.

In one embodiment the centrifugation procedure is as follows: Pour decompounded nut or seed slurry at a flow rate of 4-20 gallons per minute, for example, at a flow rate of 8 gallons per minute, into decanter centrifuge (such as the Flottweg S4 sedicanter), spinning at a bowl speed of between 3000 and 5000 RPM. Collect the liquid outflow for further use as a non-dairy milk, and set aside the ejected solids.

Other methods for removal of solids from non-dairy milks include, but are not limited to, straining, filtering, allowing to settle, skimming, or using coagulants and flocculants (including cations, polymer flocculants, or polyelectrolytes such as pectin, carrageenan, alginates, or carboxymethyl cellulose) to agglomerate particles for removal.

Centrifugation step can result in a "cream layer" and a "skim layer". The cream layer is an emulsion comprising fats, proteins and water. The skim layer is a solution comprising proteins in water. In some embodiments, the cream layer and skim layer are separated by centrifugal separation. In some embodiments, the cream layer and skim layer are separated by centrifugal separation in a Flotwegg ac1500 or GEA ME55. In some embodiments the cream layer and the skim layer are incompletely separated. The skim layer and the cream layer can be separated from the insoluble solids in a separation process. In some embodiments the skim layer and the cream layer are stored separately. The non-dairy milk can comprise the skim layer. The non-dairy milk can comprise the cream layer. Typically the skim layer and the cream layer are combined to form the non-dairy milk. The non-dairy milk can be up to 100% cream layer. In some embodiments the ratio of cream layer to skim layer in the non-dairy milk is about 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50, or 1:60. In some embodiments the methods described herein comprise measuring the amount of skim layer and cream layer being added to a non-dairy milk.

In one embodiment the separation procedure is as follows: Remove cream layer from centrifuged bucket and place in new container that is buried in an ice bath. Move the liquid layer (skim layer) from the bucket into a container that is ice cold. Keep skim and cream ice cold at all times.

In another embodiment the separation procedure is as follows: Flow the non-dairy milk, from which insoluble solids have been substantially removed by passage through a decanter centrifuge, into a separator centrifuge, for example, a Flotwegg ac1500 or GEA ME55. In some embodiments, the cream layer and skim layer are separated by centrifugal separation in the separator centrifuge. In some embodiments the separated skim and cream layers are kept refrigerated.

In some embodiments the non-dairy milk is pasteurized or sterilized. The pasteurization can be high-temperature, short-time (HTST), "extended shelf life" (ESL) treatment, or ultra-high temperature (UHT or ultra-heat-treated). In some embodiments the pasteurization procedure is as follows: Pasteurize blended non-dairy milk at 164° F.-167° F. for 16 seconds. Using controlled chilling system, bring non-dairy milk temperature down rapidly and store in a refrigerator at 36° F.

Cheese replicas may also be made using non-dairy milk prepared using proteins isolated, enriched, or purified from a plant, or microbial source or synthesized in vitro. For example ribulose-1,5-bisphosphate carboxylase oxygenase (rubisco) can isolated from a plant source and included in a non-dairy milk for the production of a cheese replica. For example 8S globulins can isolated from a Moong beans and included in a non-dairy milk for the production of a cheese replica. For example Pea globulins can isolated from Pea seeds and included in a non-dairy milk for the production of a cheese replica. For example Pea albumins can isolated from peas and included in a non-dairy milk for the production of a cheese replica. Isolated, enriched, or purified plant proteins can be combined with one or more oils or fats also isolated from plant sources, in a colloidial suspension, solution or emulsion to form the non-dairy milk for making a cheese replica. In some embodiments the isolated non-dairy proteins are combined with non-non-dairy oils or fats to form a non-dairy milk. In some embodiments multiple isolated, enriched or purified plant proteins are used to make a non-dairy milk. Without being bound by theory the non-dairy milks derived from isolated, enriched, or purified proteins may reduce the problems which can be caused by insoluble solids obtained in a slurry derived from a nut or seed. Without being bound by theory the non-dairy milks derived from isolated, enriched, or purified proteins may reduce the problems which can be caused by proteins with undesirable properties, such as lipoxygenases or proteases. Additional non-limiting examples of proteins that may be isolated, enriched, or purified from a plant source for the production of a non-dairy milk for cheese replica production include: seed-storage proteins from any seed, ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, glyceraldehyde-3-phosphate dehydrogenases, pyruvate decarboxylases, actins, translation elongation factors, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, zein, oleosins, caloleosins, steroleosins or other oil body proteins, vegetative storage protein A, vegetative storage protein B, moong seed storage 8S globulin. Non-limiting examples of oils that may be incorporated in a non-dairy milk include: corn oil, olive oil, soy oil, peanut oil, walnut oil, almond oil, sesame oil, cottonseed oil, rapeseed oil, canola oil, safflower oil, sunflower oil, flax seed oil, algal oil, palm oil, palm kernel oil, coconut oil, babassu oil, shea butter, mango butter, cocoa butter, wheat germ oil, rice bran oil, oils produced by bacteria, algae, archaea or fungi or genetically engineered bacteria, algae, archaea or fungi, triglycerides, monoglycerides, diglycerides, sphingosides, glycolipids, lecithin, lysolecithin, phophatidic acids, lysophosphatidic acids, oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, conjugated oleic acid, or esters of: oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, or conjugated oleic acid, or glycerol esters of oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, or conjugated oleic acid, or triglyceride derivatives of oleic acid, palmitoleic acid, palmitic acid, myristic acid, lauric acid, myristoleic acid, caproic acid, capric acid, caprylic acid, pelargonic acid, undecanoic acid, linoleic acid, 20:1 eicosanoic acid, arachidonic acid, eicosapentanoic acid, docosohexanoic acid, 18:2 conjugated linoleic acid, or conjugated oleic acid.

In some instances the proteins used to make the non-dairy milk may be purified proteins. Accordingly, in some embodiments the total protein content of the cheese replica can, in some embodiments, consist of greater than 25%, 50%, 75%, or 90%, of a purified protein, for example any single monomeric or multimeric protein.

Non-dairy milk compositions can also contain sugars or other fermentable carbon sources and other nutrients. Without being bound by theory these sugars or nutrients can favor growth of the cheese culture microbes or serve as substrates for production of lactic acid or other organic acids by the cheese culture microbes. For example, in some embodiments, the non-dairy milk comprises glucose. In other embodiments, the non-dairy milk comprises fructose. In other embodiments, the non-dairy milk comprises sucrose. In other embodiments, the non-dairy milk comprises high-fructose corn syrup. In other embodiments, the non-dairy milk comprises sugar-cane extract. In other embodiments, the non-dairy milk comprises a fruit juice. In other embodiments, the non-dairy milk comprises sugar-cane extract. In other embodiments, the non-dairy milk comprises agave syrup. In other embodiments, the non-dairy milk comprises molasses. Molasses can be cane molasses or beet molasses or made from other non-dairy sources. In other embodiments the non-dairy milk can comprises treacle, honey, refined sugars, or syrup (e.g high fructose corn syrup). In some embodiments fuel for glycolosis, or a component (or intermediate) of the glycolysis pathway, can be included in the compositions. Oligosaccharides can be a part of the non-dairy milk. Disaccharides (eg., maltose, sucrose) can be part of a non-dairy milk. Monosaccharides (e.g. fructose, glucose, or galactose) can be a part of the non-dairy milk. In some embodiments the sugars are added as an addition step. In some embodiments the sugars are not derived from the same organism as the proteins and fats in the composition.

In some embodiments a sugar in the composition of the invention is not treacle, honey, refined sugars, or syrup (e.g high fructose corn syrup). In some embodiments a sugar in the composition of the invention is not a monosaccharide (e.g. fructose, glucose, or galactose). In some embodiments a sugar in the composition of the invention is not a disaccharide. In some embodiments a sugar in the composition of the invention is not an oligosaccharide.

Non-dairy milk can, in some embodiments, contain one or more organic acids, such as lactic acid, or acetic acid, for example to adjust the pH and/or produce the characteristic sour taste of cheese. These organic acids may be used in addition to or as an alternative to microbial cultures. Accordingly, in some embodiments the non-dairy milk comprises an organic acid. The organic acid can be one or more of: lactic acid, acetic acid, citric acid, malonic acid, malic acid, propionic acid.

In some instances the compositions of the invention do not contain any animal products. In some embodiments the compositions of the invention use no components that are derived from animals. In some embodiments the compositions of the invention contain no fats from animals. In some embodiments the compositions of the invention contain no proteins from animals. In some embodiments the compositions of the invention contain no enzymes from animals. In some embodiments the compositions of the invention contain no dairy products.

In one embodiment the invention provides a composition free of or substantially free of one or more of the following: dairy products, animal products, agar, carrageenan, or tofu.

In some embodiments the compositions have less than 20%, less than 15%, less that 10%, less than 5%, less than 1% or less than 0.5% starch content. In some embodiments no refined starch (e.g. cornstarch, tapioca, wheat, or potato starch) is added to the compositions of the invention.

In some embodiments the non-dairy milk contains no artificial flavoring or coloring.

In some instances the non-dairy milk does contain some animal products. For example, in some embodiments, non-dairy milk comprises enzymes obtained from animals. In some embodiments, the non-dairy milk contains dairy products. In some embodiments animal fats are included in the non-dairy milk. In some embodiments the non-dairy milk can comprise enzymes (e.g. proteases and lipases), and/or microbes (e.g. lactic bacteria, yeast and mold). Without being bound by theory these enzymes and or microbes can be added to non-dairy milk formulations to produce desirable flavor and aroma compounds.

Enzymes, including proteases and lipases, and microbes, including lactic bacteria, yeast and mold, can be added to non-dairy milk formulations to produce desirable flavor and aroma compounds.

In some embodiments the invention provides a method comprising isolating or purifying a single non-dairy protein, mixing the isolated non-dairy protein with a non-dairy fat source, and adding a microorganism selected from the group consisting of *Penicillium camemberti, Geotrichum candidum, Penicilliem roqueforti, Penicillium nalgiovensis, Verticillium lecanii, Kluyveromyces lactis, Saccharomyces cerevisiae, Candida utilis, Debaryomyces hansensil, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., or *Propionibacteria*. In some embodiments at least 1 kg of the plant protein is isolated or purified from a single non-dairy source. In some embodiments the fat is isolated from another non-dairy source.

In some embodiments the invention provides for a composition comprising an isolated or purified non-dairy protein and a polynucleotide identifiable as derived from one or more of *Penicillium camemberti, Geotrichum candidum, Penicilliem roqueforti, Penicillium nalgiovensis, Verticillium lecanii, Kluyveromyces lactis, Saccharomyces cerevisiae, Candida utilis, Debaryomyces hansensil, Rhodosporidum infirmominiatum, Candida jefer, Cornybacteria, Micrococcus sps., Lactobacillus* sps., *Lactococcus, Staphylococcus, Halomonas, Brevibacterium, Psychrobacter, Leuconostocaceae, Streptococcus thermophilus, Pediococcus* sps., or *Propionibacteria*. In some embodiments the cheese replicas comprise *Penicillium camemberti, Geotrichum candidum, Penicilliem roqueforti, Penicillium nalgiovensis, Verticillium lecanii, Kluyveromyces lactis, Saccharomyces cerevisiae, Candida utilis, Debaryomyces hansensil, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., or *Propionibacteria*. In some embodiments compositions of the invention comprise *Penicillium, Geotrichum, Saccharomyces, Kluyveromyces,* or *Debaryomyces*.

II. "Curdling" the Non-Dairy Milk

Generally the cheese-replicas are made by causing cross linking or denaturation of proteins in non-dairy milks. These processes replicate the curdling process of traditional dairy cheese making.

Crosslinking is typically induced using an enzyme that creates covalent crosslinks between polypeptide chains. In some embodiments cross-linking enzymes are used in a cross-linking step to curdle the non-dairy milk. In various embodiments, transglutaminase is the cross-linking enzyme used to induce the curdling of non-dairy milk replicas. In some embodiments the crosslinking enzyme used to induce curdling in non-dairy milk replicas is a lysyl oxidase. In one embodiment, the invention provides for a method of inducing the curdling of a non-dairy milk comprising obtaining a non-dairy milk and adding a cross-linking enzyme to the non-dairy milk. In some embodiments the cross-linking enzyme is transglutaminase. In some embodiments the cross-linking enzyme is not derived from an animal source. In some embodiments the curdling process does not use rennet.

In some embodiments between 0.1 and 20 units (U) of transglutaminase is added per 1 mL of non-dairy milk. In some embodiments about 0.1, 0.5, 1, 1.5, 2, 2.5, 3, 5, 7, 10, 15, or 20 U transglutaminase is added per 1 mL of non-dairy milk. In some embodiments the transglutaminase is followed by heated incubation, for example in a 100° F. water bath. The heated incubation can be at a temperature optimized for the enzyme function. In some embodiments the temperature is about 65, 70, 75, 80, 85, 90, 95, 100, 105, 110, 115, 120 or 125° F.

Transglutaminases are a family of enzymes that catalyze the formation of a covalent bond between a free amine and the gamma-carboxyl group of glutamine thereby linking proteins together. For example, transgluaminases catalyze crosslinking of e.g., lysine in a protein or peptide and the gamma-carboxamide group of a protein- or peptide-glutamine residue. The covalent bonds formed by transglutaminase exhibit high resistance to proteolytic degradation.

Many types of transglutaminase can be used in various embodiments of the invention. Acceptable transglutaminases include, but are not limited to, *Streptoverticillium mobaraense* transglutaminase, an enzyme is similar or identical to a transglutaminase from *Streptoverticillium mobaraense*, other microbial transglutaminases, transglutaminases produced by genetically engineered bacteria, fungi or algae, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), TGM Z (TGM7), or lysyl oxidase. Accordingly, in some embodiments an enzyme selected from the group consisting of a transglutaminase is used to crosslink a non-dairy milk protein. In some embodiments the transglutaminase is *Streptoverticillium mobaraense* transglutaminase, other microbial transglutaminases, transglutaminases produced by genetically engineered bacteria, fungi or algae, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), TGM Z (TGM7), or lysyl oxidase In some embodiments the present invention provides for a composition comprising a non-dairy milk and *Streptoverticillium mobaraense* transglutaminase, an enzyme is similar or identical to a transglutaminase from *Streptoverticillium mobaraense*, other microbial transglutaminases, transglutaminases produced by genetically engineered bacteria, fungi or algae, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6) and/or TGM Z (TGM7). In some embodiments the enzyme used for cross-linking is not Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), TGM Z (TGM7), or lysyl oxidase.

In some embodiments the invention provides for a composition comprising a non-dairy milk, wherein the composition is free of Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6) and/or TGM Z (TGM7).

Transglutaminases can be produced by *Streptoverticillium mobaraense* fermentation in commercial quantities or extracted from animal tissues. Additionally, the transglutaminase (TGM) of the present invention may be isolated from bacteria or fungi, expressed in bacteria or fungi from a synthetic or cloned gene, Factor XIII, keratinocyte transglutaminase, tissue transglutaminase, epidermal transglutaminase, prostate transglutaminase, TGM X, TGM Y, TGM Z, or another member of the transglutaminase family. In some particular embodiments transglutaminase is obtained from commercial sources, for example in the form of Activa™ from Ajinmoto Food Ingredients LLC.

In some embodiments the compositions of the invention have a detectable amount of a nucleic acid from the genome of a cell that encoded and produced an enzyme, for example a transglutaminase. For example a cheese replica can have a detectable amount of *Streptoverticillium mobaraense* DNA. This detectable amount can, for example, be a small amount of DNA that has carried over to the cheese replica from the production of transglutaminase by *Streptoverticillium mobaraense*.

In some embodiments the cross-linking of proteins in non-dairy milk is induced by transglutaminase. In some embodiments the cross-linking of proteins in non-dairy milk is induced by a lysyl oxidase. Various non-dairy milks have been crosslinked with transglutaminase. In some embodiments the invention provides a composition comprising a non-dairy milk and transglutaminase. In some embodiments the invention provides a composition comprising a curdled non-dairy milk and transglutaminase. In some embodiments the invention provides a cheese replica containing transglutaminase. In some embodiment the invention provides a cheese replica with a detectable amount of degraded transglutaminase. In some embodiment the invention provides a cheese replica with a detectable amount of improperly folded transglutaminase. In some embodiment the invention provides a cheese replica with a detectable amount of transglutaminase by-product. In some embodiment the invention provides a cheese replica with a detectable peptide which is identifiable as portion of a transglutaminase used in the manufacturing process for making the cheese replica. In some embodiment the invention provides a cheese replica with one or more detectable peptides containing a crosslink between a lysine and glutamine residue. For example the crosslinked glutamine and lysine residues may be detectable by mass spectroscopy. In some embodiment the invention provides a cheese replica with one or more detectable peptides containing a crosslink between two lysine residues. For example the crosslinked lysine residues may be detectable by mass spectroscopy.

Denaturation can be used instead of, or in addition to, the cross-linking enzyme for curdling the non-dairy milk. For example, heat denaturation of a non-dairy milk followed by cooling of the mixture can result in a curd-like gel as, for example, described in example 7. Accordingly, the present invention provides for non-dairy milk curds comprising denatured non-dairy proteins. The present invention also provides for methods for making a non-dairy milk curd by heating a non-dairy milk to a temperature of about between 30-35, 35-40, 40-45, 45-50, 50-55, 55-60, 60-65, 65-70, 70-75, 75-80, 80-85, 90-95, 95-100° C. for about 10, 20, 30, 40, 50, 60 seconds or about 1, 2, 3, 4, 5, 6, 7, 8, 9, or 10 minutes followed by cooling. In some embodiments non-dairy milks are curdled using both enzymatic cross-linking with transglutaminase and heat denaturation.

Additional denaturization procedures are possible in additional embodiments of the invention. Acids, solvents, chaotropic agents, or disulfide bond reducers can be used to denature the proteins in the non-dairy milk. In one embodiment urea is added to the non-dairy milk to form curds.

III. Cheese Replica Production from the Curdled Non-Dairy Milk

Cheese replicas can be produced from the curdled non-dairy milk. Accordingly, the invention provides methods for producing cheese replicas from curdled non-dairy milk, as well as cheese replica compositions.

To create the cheese replicas one might use elements of the traditional cheese making process. Cheese replicas can be produced using one or more steps including cutting, draining, forming, pressing, waxing, aging, scalding, smoking, salting or ripening.

The curd and whey may be separated in a traditional way. For example, the cheese may be scalded to create a replica of traditional cheddar or other hard cheese, or, the whey and curd might be separated through a cloth drain.

The cheese replicas may be ripened in a way similar to traditional cheese. For example, surface mould may be allowed to grow to create a rind. In order to create a rind or color, the process may introduce certain bacteria to the cheese replicas in the ripening process. By way of example only, *Brevibacterium linens* can be introduced to produce an orange color and pungent aroma to the cheese replica.

In some embodiments, the cheese replica can be a salted or salt-washed cheese replica. The salting process can preserve the cheese replica and/or add flavor. In some embodiments the salt is chosen based on the geographic location of where the salt is originally obtained. In some embodiments salt is added to the cut curds. In some embodiments salt is contacted with the outside surface of the cheese replica, for example by rubbing. In some embodiments the cheese replica is contacted with or soaked in brine.

In some embodiments, the cheese replica can be a soft fresh cheese produced by procedures exemplified by example 3.

In some embodiments, the cheese replica can be a salted or salt-washed cheese produced by procedures exemplified by example 4.

In some embodiments, the cheese replica can be a soft ripened or molded-rind cheese produced by procedures exemplified by example 5.

In some embodiments, the cheese replica can be a goat cheese replica produced by procedures exemplified by example 6.

In some embodiments, the cheese replica can have edible materials added (e.g. herbs, pepper, spices) on its surface to enhance flavor or add to the visual appeal of the product, as exemplified by examples 4 and 6. In some embodiments the edible materials are embedded in the cheese replica.

In some embodiment the cheese replica can be shaped. For example the cheese replica can be shaped in a basket or a mold. In some embodiments the cheese replica is pressed, for example with a weight. The pressing can help expel any additional liquid from the cheese replica.

In some embodiments the production of the cheese replica includes a waxing step. In one embodiment the waxing procedure is as follows: Cut food-grade paraffin wax into ½-inch pieces. Place in double boiler and heat wax to 210° F. Place cheese replicas in standard freezer for fifteen minutes to reduce temperature of cheese replicas to 33° F. Using 3-grams of melted wax per piece, brush wax onto cheese replicas one side at a time. Placed waxed cheese replicas onto clean waxed paper on aging racks. Age waxed cheese replicas in aging room at 36° F. with 75% humidity, for example for six months. In some embodiments the aging room is between 33-70° F. In some embodiments the humidity of the aging room is altered to aid in rind formation. In some embodiments the waxed cheese is stored for years, for example for 2 years or more.

In some embodiments the production of the cheese replica includes a smoking step. In some embodiments the cheese replica is cold smoked. In some embodiments the cheese replica is smoked at the curd stage or prior to the curd stage. In some embodiments the cheese replica is smoked after the cheese replica is formed. In some embodiment the smoking procedure is as follows: Soak wood chips for six hours. Drain chips of all water and place in smoking unit. Ignite smoker and as soon as chips have fully ignited, snuff out flames to create smoke-filled unit. Place cheese replicas on racks in smoker for five minutes per side. Remove from smoker and place on cooling racks. Place cheese replicas in cooling room for 24 hours, at 36° F. In various embodiments smoking times and cooling times and temperatures will be adjusted according to the particular cheese replica and particular desired taste profile.

In some instances the cheese replica is exposed to or injected with mold or yeast. In some embodiments the cheese replica is exposed to a particular bacterial strain or strains.

When the cheese replica is made without any dairy ingredients, the production process requires no dairy farming. Accordingly, the process for making cheese replicates is suitable for locations where keeping animals or storing milk is difficult or costly. In some embodiments the cheese replicas are made in non-dairy producing regions. This will reduce the need for shipping the products. So in some embodiments the cheese replica is a product that is made in the same locality as its eventual consumption. For example the cheese replica is made within 10, 20, 50, or 100 miles of its point of sale. The cheese replica production process may also be useful in remote areas where dairy farming is difficult or impossible. For example the cheese replica production process could occur on an island, aboard an oil platform, or aboard a space station.

The cheese replicas may further contain microbes useful for cheese making. So in some embodiments the cheese replicas may be made by a process involving culturing with any microbes used for cheese making. The cheese replicates may be made by a process involving fermentation. In any process, the proteins may be crosslinked by treatment with an enzyme, which may be from the family of transglutaminase. The cheese replicas may be created from curds formed by a treatment of a protein-containing liquid with a transglutaminase, or other enzymes that promote gelling, or they may be prepared by a process involving heat denaturation of one or more of the protein components in the solution, suspension or emulsion to induce formation of a gel.

In some embodiments the cheese replicas comprise *Penicillium, Geotrichum, Saccharomyces, Kluyveromyces*, or *Debaryomyces*.

IV. Non-Dairy Cheese Replicas

The cheese replicas can be made for consumption by either humans or other animals or both. In some instances the cheese replicas are used to feed domesticated animals. For example, a cheese replica of the present invention can be fed to a dog. In one particular embodiment, the cheese replica contains a veterinary medication In another embodiment the cheese replica comprises a treat for a domestic animal. In some embodiments the domestic animal treat is shaped like traditional a wedge of cheese. In some embodiments the animal treat is artificially colored to resemble dairy cheese, e.g. cheddar cheese.

The cheese replicas include products similar to conventional cheese, yogurt and other dairy products. Cheese replica can be made from a liquid extract of nuts or other fruits or seeds. The current invention also includes cheese replicas made from proteins and fats isolated and enriched or purified from one or more plant. The current invention also includes cheese replicas made from proteins and fats isolated and enriched or purified from one or more non-dairy source.

In some embodiments the cheese replica has less than 1%, 5%, 10%, 20%, 25% or 30% polysaccharides.

In some embodiments the cheese replica has less than 1%, 5%, 10%, 20%, 25% or 30% polysaccharides because of centrifugal separation.

In some embodiments the cheese replica has less than 1%, 5%, 10%, 20%, 25% or 30% polysaccharides because of the use of purified proteins.

The cheese replicas may be suitable for consumption by humans or animals who are unable to eat certain animal products, such as a person who is lactose-intolerant or allergic to dairy. Accordingly, in some embodiments the cheese-replica does not contain lactose. The cheese replicas might contain enough protein or other nutrients to be nutritionally equivalent to traditional cheese or other animal products.

The cheese replicas may contain less fat, less saturated fat or less cholesterol than traditional cheese or animal products, and may be suitable for a healthier diet. So in some embodiments provided herein is a method for distributing cheese replicas comprising the steps of informing a lactose intolerant person of the cheese replica, receiving an order for a cheese replica, and making the cheese replica available to the lactose intolerant person.

In some embodiments the lactose intolerant person is informed through advertising. In some embodiments the lactose intolerant person is informed by their personal physician. In some embodiments the order for the cheese replica is sent by the lactose intolerant person. In some embodiments the lactose intolerant person receives the cheese replica via a distributor that places the order. In some embodiments the informing and receiving steps take place on a network, for instance a computer network and are enacted with specialized computer software stored on a computer readable media. In some embodiments the method further comprises producing a cheese replica of the present invention and supplying it to lactose intolerant person.

The cheese replicas are, in some embodiments, designed to replicate the experience of eating cheese. The look, texture, and taste of the cheese replicas can be such that it is similar or indistinguishable from cheese. The invention provides for methods for determining whether a animal or human can distinguish the cheese replicas from cheese. In some embodiments a property of the compositions of the invention is that an animal, for example a human, will identify the composition as cheese. In some embodiments the human identifies the composition of the invention as equivalent to cheese. In some embodiments one or more properties of cheese are equivalent according to an ordinary human's perception. Such properties include the properties that can be tested listed below. In some embodiments an ordinary human identifies a cheese replica of the present invention as more cheese like than cheese substitutes found in the art.

One method to determine whether the cheese replica is comparable to cheese is to a) define the properties of cheese and b) determine whether the cheese replicas has similar properties. Properties of cheese that can be tested include mechanical properties such as hardness, cohesiveness, brittleness, chewiness, gumminess, viscosity, elasticity, and adhesiveness. Properties of cheese or a cheese replica that can be tested also include geometric properties such as particle size and shape, and particle shape and orientation. Additional properties can include moisture content and fat content. The properties of the cheese replica can be described using terms such as "soft," "firm" or "hard" describe hardness; "crumbly," "crunchy," "brittle," "chewy," "tender," "tough," "short," "mealy," "pasty," or "gummy," to describe cohesiveness; "thin" or "viscous" or "spreadable" to describe viscosity; "plastic" or "elastic" to describe elasticity; "sticky," "tacky" or "gooey" to describe adhesiveness; "gritty," "grainy" or "coarse" or "heterogeneous" to describe particle shape and size; "fibrous," "cellular" or "crystalline" to describe particle shape and orientation, "dry," "moist," "wet," or "watery" to describe moisture content; or "oily" or "greasy" to describe fat content. In one embodiment a group of people can be asked to rate a certain cheese, for instance cheddar, according to properties which describe the cheese. These ratings can be used as an indication of the properties of the cheese. The cheese replicas of the present invention can then be compared to the properties of traditional dairy cheese to determine how similar the cheese replica is to the dairy cheese. In some instances the properties of the cheese replicas are then altered to make the cheese replica more similar to the cheese. In some embodiments, the cheese replica has a property or properties that are rated similar to cheese according to human evaluation. In some embodiments the cheese replica is indistinguishable from real cheese to a human. In some embodiments the cheese replica is distinguishable by some properties from real cheese to a human.

In some embodiments the cheese replica is compared to real cheese based upon olfactometer readings. In various embodiments the olfactometer can be used to assess odor concentration and odor thresholds, odor suprathresholds with comparison to a reference gas, hedonic scale scores to determine the degree of appreciation, or relative intensity of odors. In some embodiments the olfactometer allows the training and automatic evaluation of expert panels. In some embodiments the cheese replica is a product that causes similar olfactometer readings to those of a particular target cheese. In some embodiments the cheese replica is a product that causes nearly similar, but slightly different olfactometer readings to those of a particular target cheese.

Gas chromatography-mass spectrometry (GCMS) is a method that combines the features of gas-liquid chromatography and mass spectrometry to identify different substances within a test sample. GCMS can, in some embodiments, be used to evaluate the properties of a cheese replica. For example volatile chemicals can be isolated from the head space around cheese. These chemicals can be identified using GCMS. A profile of the volatile chemicals in the headspace around cheese is thereby created. In some instances each peak of the GCMS can be further evaluated. For instance, a human could rate the experience of smelling the chemical responsible for a certain peak. This information could be used to further refine the profile. GCMS could then be used to evaluate the properties of the cheese replicas. The GCMS could be used to refine the cheese replica. In some embodiments the cheese replica has a GCMS profile similar to that of cheese. In some embodiments the cheese replica has a GCMS profile identical to that of cheese.

The cheese replicas may be modified to fit into traditional cheese-types, including: fresh, bloomy, semi-soft, washed, firm, hard and blue. There may be additional processes to modify the cheese replicas and fit them into any cheese-type category. These categories also include different presentations of the cheese replicas, for example: sliced, shredded, block, with rind, without rind, wet or dry. The cheese replicas may be aged, or a method may be created to mimic the taste of traditionally-aged dairy cheese. The cheese replicas may be classified in taste the same way traditional cheese is. For example, they may be tart, tangy, smooth, creamy, buttery, fluffy, rich, earthy, pungent, aromatic, eggy, fruited, sharp, dry, caramelly, grainy, punchy or complex, among other descriptions. The invention includes methods to modify the cheese replicas to fit into any category or taste description.

The cheese replicas may be modified to have or not have a rind, may be coated in wax, and may have craters or veins typical to blue cheese. The cheese replicas may be spreadable, such as cream cheese. The cheese replicas can contain flavor additives, for example: truffle, mushrooms, nuts, herbs, chives, and other flavors.

The cheese replicas may be meltable, and have other properties of conventional cheese.

The cheese replicas may also be similar in consistency and taste to traditional yogurt or cottage cheese. The cheese replicas might be flavored with fruits, sweeteners, or other flavor additives. The cheese replicas might contain bacteria to aid with digestion or other health additives. The cheese replicas may be modified to have an appropriate or appealing consistency.

In various embodiments the cheese replicas may be used in all cooking and recipes as a substitute for traditional cheese. In some embodiments the cheese replicas may be used in cooking and recipes as a flavor substitute for traditional cheese. In some embodiments the cheese replicas may be used in cooking and recipes as a functional substitute for traditional cheese.

EXAMPLES

Example 1

The Effectiveness of Transglutaminase in Curdling Various Nut Milks was Compared Cashews, almonds, macadamia nuts, brazil nuts were used to produce a slurry, by adding fresh water in a 3:1 weight ratio to the nuts, then blending in a Vitamix 4500 blender at high speed for 2 minutes. Because we found in preliminary experiments that the insoluble solids in the milks at this stage (slurry) inhibited formation of optimal creamy curds and produced a cheese replica with grainy mouth feel the slurry was subjected to centrifugation at 10,000 G for 15 minutes at 4° C. to remove insoluble solids. The liquid supernatant, consisted of two layers, a lighter, creamy, opaque layer and a slightly denser clear to translucent aqueous layer. Liquid supernatant layers were recovered and blended together and the pelleted solids were discarded. The blended supernatants are referred to as "nut milks" (a non-dairy milk). Each of the 4 resulting nut milks and each pair-wise combination at a 1:1 blend, were evaluated for curdling in the presence of transglutaminase (TG): 30 U TG was added to 15 mls of each nut milk or blend in a 20 ml glass vial, followed by incubation in a 100° F. water bath. After 5 hours all but the pure cashew nut milk had formed sturdy curds, sufficient to retain their form when the glass vial was inverted. The cashew milk and cashew brazil nut milks formed soft curds. The macadamia and almond milks formed the most solid curds. Control samples without added transglutaminase remained liquid under these conditions.

Example 2

Preparation of Almond and Macadamia Nut Milks

Blanching (Surface Sterilization of the Nuts):
Note: Almonds and macadamia nuts were blanched separately.
A 30 gallon tilt skillet filled to ½-capacity with fresh water was heated to 212° F. 25 pounds of either almonds or macadamia nuts were dumped into the boiling water bath and left for 30 seconds. The nuts were recovered by draining into a colander then immediately immersed in fresh ice-cold water in a second tilt skillet to rapidly cool them. After rapid cooling the nuts were recovered by draining in a colander and spread on sheet trays to dry.
Macadamia nuts proceeded directly to the blending process. Almonds were first hydrated as described below before blending.
Hydration of Almonds:
The blanched almonds were transferred to Cambro buckets and fresh water was added to a level two inches above the level of the nuts. The buckets were then placed at 36° F. for up to 16 hours. After hydration, the nuts were recovered by draining into a colander, rinsed with fresh water, then proceeded to the blending step.
Blending of Nuts:
Note: Almonds and macadamia nuts were blended separately.

One pound batches of nuts were placed in a Vitamix blender (model Vitaprep 3), with one liter of fresh water and blended for 5 minutes, gradually increasing the blender speed to high. The blended slurries from each batch were collected in a stainless steel bain-marie sitting in a large container of ice and stirred with a frozen cooling stick to cool. Once the accumulated slurry cooled to 50° F., the bain-marie was placed in a refrigerator at 36° F. for up to 12 hours.
Separation of Skim and Cream:
Sets of four 1800 ml aliquots of the blended slurry were centrifuged at 5000 RPM/7480 G at 4° C. for 30 minutes in a Beckman-Coulter Avanti J-HC Centrifuge with a JS-5.0 rotor, resulting in separation of the blend into 3 layers, a dense pellet of insoluble solids, a clear to translucent aqueous layer (which we refer to as the "skim"), and a lighter, creamy, opaque layer (which we refer to as the "cream"). The cream layer was carefully collected from each bucket using a spoon, and placed in a pan sitting in a container of ice. The viscous aqueous layer (skim) from each bucket was carefully poured into a ½-Cambro sitting in a container of ice. The accumulated cream and skim layers were kept at 36° F. until the pasteurization step. Typical yields were about 0.77 lbs of cream and 0.95 lbs of skim per lb of macadamia nuts and about 0.29 lbs of cream and 1.62 lbs of skim per lb of almonds.
Blending
Almond skim and cream were combined in a ratio specified by the recipe for the specific cheese replica being produced (Table 1), and blended with an immersion blender. Macadamia skim and cream were combined in a ratio specified by the recipe for the specific cheese replica being produced (Table 1), and blended with an immersion blender. We hereafter refer to each blended mixture of skim and cream as "non-dairy milk." The two non-dairy milks were then blended in a ratio specified by the recipe for the specific cheese replica being produced (Table 1).
Pasteurization:
The non-dairy milk blend was pasteurized at 167° F. for 16 seconds after which the non-dairy milk temperature was rapidly reduced to 50° C. in 12 seconds by a controlled chilling system. The non-dairy milk temperature was then further reduced by placing containers in an ice bath at 36° F. Pasteurized non-dairy milks were stored at 36° F. Non-dairy milks were discarded if the pH of the non-dairy milk dropped below pH 6.0 during storage, indicating spoilage.

Example 3

Production of a Soft Fresh Cheese Replica

The ingredients and amounts needed for one batch (about one and a half pieces) of soft fresh cheese replica are listed in Table 2. The recipe can be scaled up or down proportionately.
Soft fresh cheese replica was prepared by the following procedure:
non-dairy
Bring pasteurized non-dairy milk formula (see Table 2) to 80° F. in a water bath.
Sprinkle the mesophilic starter culture (see Table 2) onto the non-dairy milk formula and allow the culture to hydrate for five minutes without stirring. Gently stir in the starter culture with a spatula for two minutes. Hold at 80° F. for one hour.
Increase the water bath temperature to begin to bring the non-dairy milk temperature to 100° F.

Optional step: Add microbial "rennet" and/or distilled vinegar (see Table 2), folding gently with a spatula. Hold for 15 minutes.

Dilute the hydrated transglutaminase (see Table 2) with a small amount of warm non-dairy milk formula and then add it to the non-dairy milk formula, folding gently with a spatula for two minutes. Allow formula to reach 100° F.

Remove the container of non-dairy milk formula from the water bath and cover with plastic wrap and aluminum foil. Allow the non-dairy milk formula to coagulate for twelve hours at room temperature.

Cut curd into ½ inch dice pieces. (FIG. 1). Allow curd to re-mat for 10 minutes. Pour the coagulated formula (curd and whey) into a draining bag and measure its weight. Hang bag and allow curd to drip for a minimum of 20 minutes until proper viscosity and density of curd is achieved. The drained curd should weigh about 60% of original formula weight.

Place curd in a mixing bowl. Add cheese salt (see Table 2). Gently whisk the curd for ten minutes, or blend for five minutes with a Hobart mixer on low to medium speed.

Figure 2:
FIG. 2 shows drained curds prepared by the method used to produce the soft fresh cheese replicas and salted cheese replicas described in the examples.

Place 13.75 ounces of curd (enough to yield eight ounces after completion of draining and brining) (FIG. 2) into a micro-perforated mold. Drain at room temperature for one hour without the follower in place. Then place the follower in the mold and add 600 grams of weight to the follower. Refrigerate at 36° F. for 24 hours.

Preheat saturated brine to 50° F. Fully immerse the cheese replica, still in its mold, into the preheated brine for ½ hour. After brining, place mold on draining rack and return it to 36° F. for 24 hours.

Remove cheese replica from the mold. Place on draining mat and return it to 36° F. for 24 hours.

Figure 3:
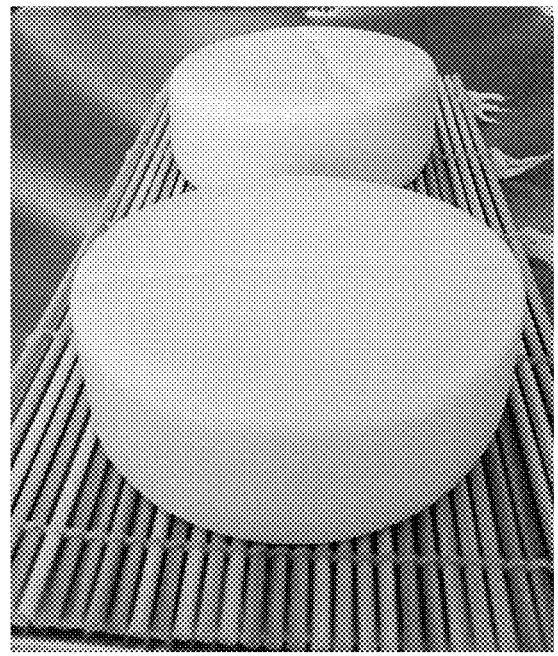
FIG. 3 shows soft fresh cheese replicas made from non-dairy milk.

The soft fresh cheese replica (FIG. 3) is now ready for packaging and shipment. Packaging process includes nitrogen flush and airtight heat-sealing.

Example 4

Production of a Salted Cheese Replica

The ingredients and amounts needed for one batch (about one and a half pieces) of salted cheese replica are listed in Table 2. The recipe can be scaled up or down proportionately.

Bring pasteurized non-dairy milk formula (see Table 2) to 80° F. in a water bath.

Sprinkle the mesophilic starter culture (see Table 2) onto the non-dairy milk formula and allow the culture to hydrate for five minutes without stirring. Gently stir in starter culture with a spatula for full two minutes. Hold at 80° F. for one hour.

Increase water bath temperature to begin to bring non-dairy milk temperature to 100° F.

Optional: Add microbial "rennet" and/or distilled vinegar (see Table 2), folding gently with a spatula. Hold for 15 minutes.

Dilute the hydrated transglutaminase (see Table 2) with a small amount of warm non-dairy milk formula and then add it to the non-dairy milk formula, folding gently with a spatula for two minutes. Allow formula to reach 100° F.

Remove container of non-dairy milk formula from the water bath and cover. Allow the non-dairy milk formula to coagulate for twelve hours at room temperature.

Cut curd into ½ inch dice pieces (see FIG. 1). Allow curd to re-mat for 10 minutes. Pour the coagulated formula (curd and whey) into a draining bag and measure its weight. Hang bag and allow curd to drip for a minimum of 20 minutes until proper viscosity and density of curd is achieved. The drained curd should weigh about 60% of original formula weight.

Figure 5:
FIG. 5 shows salted cheese replica made from non-dairy milk.

Place curd in mixing bowl. Optional: For the classic presentation of a cheddar cheese replica (FIG. 5), annatto—a natural vegetable dye, is added to create the yellow cheddar color. The percentage of annatto evenly distributed throughout the curd is 0.08%. Gently whisk curd for ten minutes, or blend for five minutes with a Hobart mixer on low to medium speed.

Place 16.3 ounces of curd (enough to yield eight ounces after completion of draining and brining) (see FIG. 2) into a micro-perforated mold. Drain at room temperature for one hour without the follower in place. Then place the follower in the mold and add 600 grams of weight to the follower. Refrigerate at 36° F. for 24 hours.

Preheat saturated brine to 50° F. Fully immerse the cheese replica, still in its mold, into the preheated brine for ½ hour. After brining, place mold on draining rack and return it to 36° F. for 24 hours.

Remove the cheese replica from the mold. Place the cheese replica on a draining mat and return it to 36° F. for 24 hours.

Move the cheese replica into a drying room for seven days at 55° F., with 55% humidity, and minimal airflow. Turn the cheese replica and place on a fresh draining mat daily.

Figure 4:
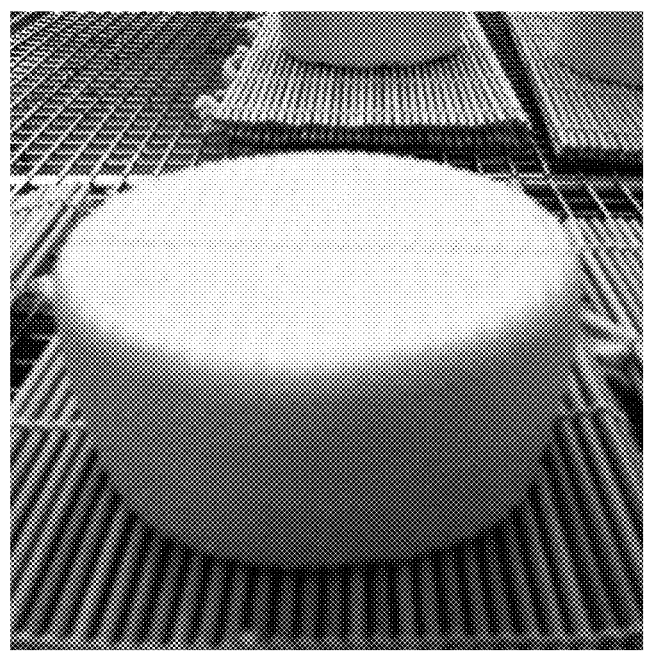
FIG. 4 shows Annatto-colored cheese replicas made from non-dairy milk.

After the seven-day drying period, remove the draining mats and place the salted cheese replica (FIGS. 4 and 5) directly on an aging rack.

If the cheese replica is to be waxed or smoked, return the cheese replica to the drying room for two additional weeks at 55° F., with 55% humidity and minimal airflow. Then follow the procedure for waxing or smoking.

If the cheese replica is to be rolled in paprika and fennel pollen mixture, follow the steps for the paprika & fennel pollen process.

Paprika and Fennel Pollen Process:

Brush the salted cheese replica with cold water using a pastry brush. Roll the cheese replica in 1.5 grams of a mixture of 10-parts organic paprika and 1-part fennel pollen. Place the coated cheese replica on an aging rack and return it to the drying room for two weeks at 55° F., with 55% humidity and minimal airflow, turning daily.

Figure 6:
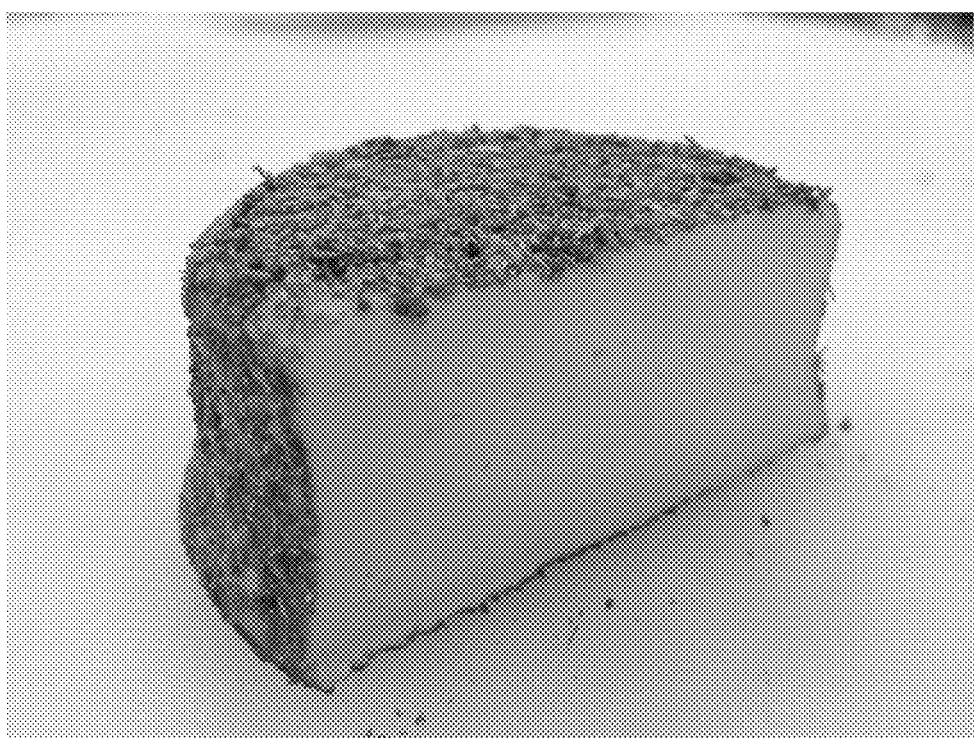
FIG. 6 shows salted cheese replica with paprika and fennel pollen made from non-dairy milk.

Following the drying period, move the cheese replica to 36° F. for 24-hours. The paprika-fennel pollen cheese replica (FIG. 6) is now ready for packaging and shipment.

Waxing Process:

Cut food-grade paraffin wax into ½-inch pieces and heat to 210° F. in a double boiler.

Figure 7:
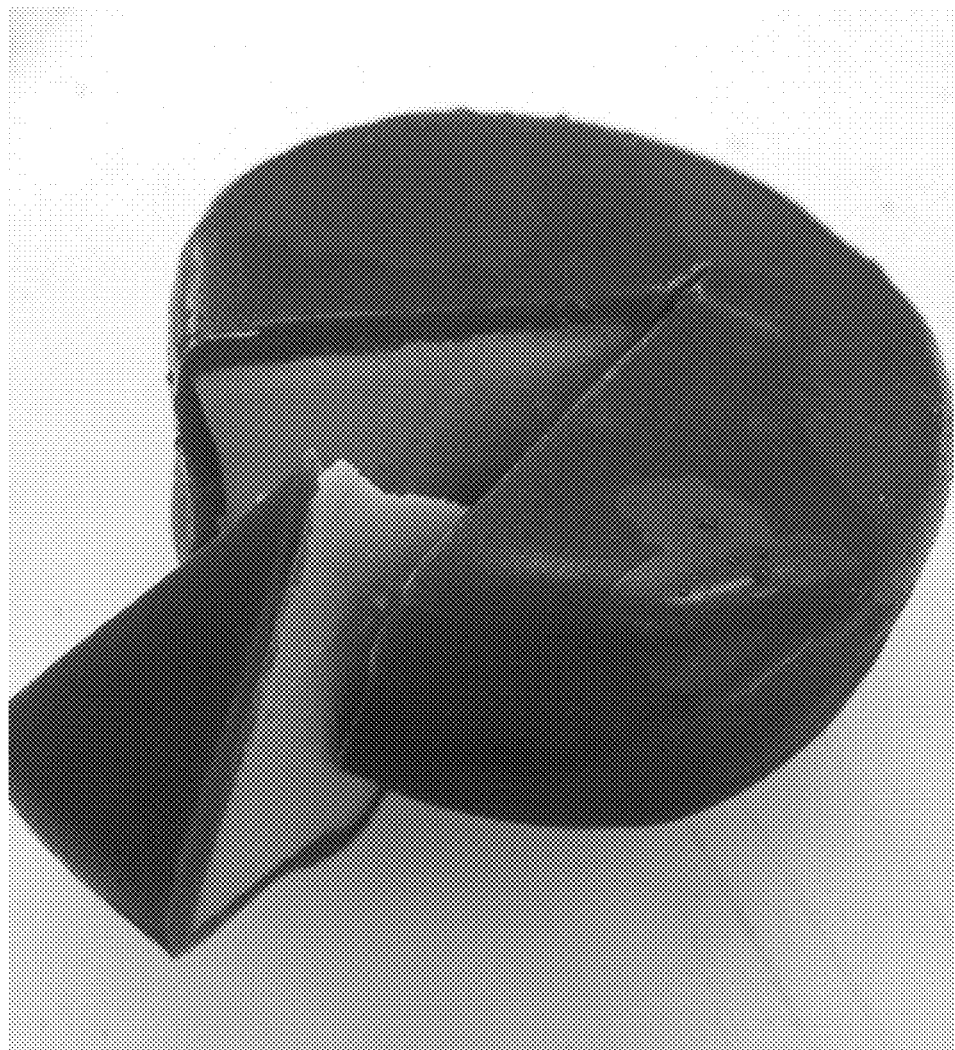
FIG. 7 shows waxed cheese replica made from non-dairy milk.

Place the cheese replica in a freezer to reduce its temperature to 33° F. Using three grams of melted wax per piece of cheese replica, brush wax onto cheese replica one side at a time. Place waxed-side down onto waxed paper and then continue brushing remainder of the cheese replica including sides and top. Placed waxed cheese replica (FIG. 7) onto clean waxed paper on an aging rack.

Age the waxed cheese replica in aging room at 36° F. with 75% humidity for up to six months. The waxed cheese replica is now ready for packaging and shipment.

Smoking Process:

Soak equal parts apple and cherry wood chips for six hours. Drain chips of all water and place in a smoking unit. Ignite smoker and as soon as chips have fully ignited, snuff out flames to create a smoke-filled unit. Place salted cheese on rack into smoker for five minutes per side. Remove cheese from smoker and place on cooling rack.

Place the cheese at 36° F. for 24 hours. Smoked cheese is now ready for vacuum aging or packaging and shipment.

Example 5

Production of a Soft Ripened Cheese Replica

The ingredients and amounts needed for one batch (about one and a half pieces) of soft ripened cheese replica are listed in Table 2. The recipe can be scaled up or down proportionately.

Bring pasteurized non-dairy milk formula (see Table 2) to 90° F. in a water bath.

Sprinkle lactose-free preparations of Florica Danica, Mesophilic Starter, *Geotrichum Candidum, Penicillium Candidum*, and *Debaromyces hansenii* (see Table 2) onto the milk formula. Optional: Add microbial "rennet." (see Table 2). Let milk sit for 5 minutes. Gently fold in and top stir with a spatula for two minutes. Hold at 90° F. for 90 minutes.

Increase water bath temperature to start to bring non-dairy milk temperature up to 100° F.

Optional: Add in distilled vinegar (see Table 2), folding gently with spatula. Hold 15 minutes.

Dilute the hydrated transglutaminase (see Table 2) with a small amount of warm non-dairy milk formula and then add it to the non-dairy milk formula, folding gently with a spatula for two minutes. Allow formula to reach 100° F.

Remove container of non-dairy milk formula from the water bath and cover with plastic wrap and aluminum foil. Allow the non-dairy milk formula to coagulate for twelve hours at room temperature.

Cut curd into ½ inch dice pieces (see FIG. 1). Allow curd to re-mat for 10 minutes. Pour the coagulated formula (curd and whey) into a draining bag and measure its weight. Hang bag and allow curd to drip for a minimum of 20 minutes until proper viscosity and density of curd is achieved. The drained curd should weigh about 60% of original formula weight.

Place curd in mixing bowl. Add cheese salt. Gently whisk curd for ten minutes, or blend for five minutes with a Hobart mixer on low to medium speed.

Place 17.64 ounces (500 grams) of curd (enough to yield eight ounces after completion of draining and brining) (FIG. 2) into a micro-perforated mold on a draining mat. Drain at room temperature for one hour without the follower in place. Then place the follower in the mold just touching the cheese replica. Do not add any additional weight to the follower. Refrigerate at 36° F. for 24 hours.

Preheat saturated brine to 50° F. Fully immerse the cheese replica, still in its mold, into the preheated brine for ½ hour. After brining, place mold on draining rack and return it to 36° F. for 24 hours.

Remove the cheese replica from the mold. Place on draining mat and return it to 36° F. for 24 hours.

Transfer the cheese from 36° F. to dry yeasting room for three days at 60° F., with 75% humidity.

After three days, transfer cheese from a draining mat to an aging mat. Place the mat on an aging rack, and move to ripening room at 50° F., with 90% humidity and continuous airflow. Turn the cheese replica and replace mat daily.

After seven days, transfer the cheese replica directly onto an aging rack, allowing maximum aeration for seven more days, or until mold coverage is complete.

Figure 8:
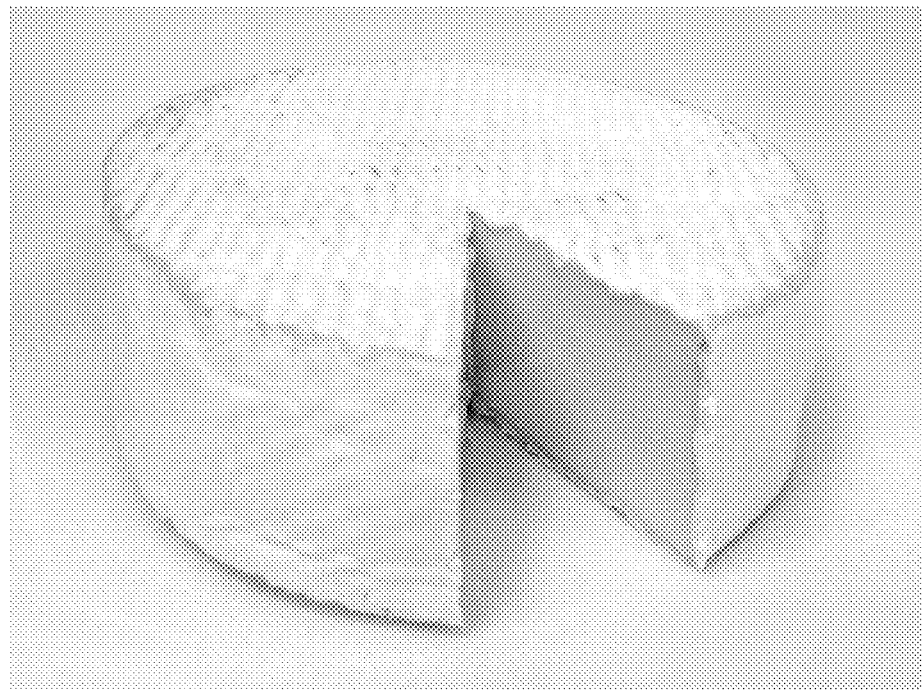
FIG. 8 shows soft ripened cheese replica made from non-dairy milk

After the cheese replica is thoroughly covered with mold (FIG. 8), move it to 36° F. for sixteen hours. Wrap cheese in perforated paper and place in a wooden box for shipment.

Example 6

Production of a Goat Cheese Replica

The ingredients and amounts needed for one batch (about one and a half pieces) of goat cheese replica are listed in Table 2. The recipe can be scaled up or down proportionately.

Bring pasteurized milk formula (see Table 2) to 80° F. in a water bath.

Sprinkle the mesophilic starter culture (see Table 2) onto the non-dairy milk formula and allow the culture to hydrate for five minutes without stirring. Gently stir in starter culture with a spatula for full two minutes. Hold at 80° F. for one hour.

Increase water bath temperature to begin to bring non-dairy milk temperature to 100° F.

Optional: Add microbial "rennet" and/or distilled vinegar (see Table 2), folding gently with a spatula. Hold for 15 minutes.

Dilute the hydrated transglutaminase (see Table 2) with a small amount of warm non-dairy milk formula and then add it to the non-dairy milk formula, folding gently with a spatula for two minutes. Allow formula to reach 100° F.

Remove container of non-dairy milk formula from the water bath and cover with plastic wrap and aluminum foil. Allow the non-dairy milk formula to coagulate for twelve hours at room temperature.

Cut curd into ½ inch dice pieces. Allow curd to re-mat for 10 minutes. Pour the coagulated formula (curd and whey) into a draining bag and measure its weight. Hang bag and allow curd to drip for a maximum of 24 hours until proper viscosity and density of curd is achieved. The drained curd should weigh about 50% of original formula weight.

Place curd in mixing bowl. Add cheese salt (see Table 2). Using Hobart mixer on high speed, mix and aerate completely.

Place sixteen ounces of curd (enough to yield eight ounces after completion of draining and brining) (FIG. 2) into a cylindrical goat cheese mold and stand the mold upright on a draining mat. Refrigerate at 36° F. for 24 hours allowing the cheese replica to drain.

Preheat saturated brine to 50° F. Fully immerse the cheese replica, still in its mold, horizontally into the preheated brine for ½ hour.

After brining, stand mold on draining mat placed at 36° F. for 24 hours. Turn mold and change mat every twelve hours for two days.

Slide shaped goat cheese replica out of mold directly onto a bed of three grams of coarse ground pepper. Gently roll the cheese replica in pepper, covering evenly and completely. Place the cheese replica on waxed paper and return to 36° F. for 48 hours.

Figure 9:
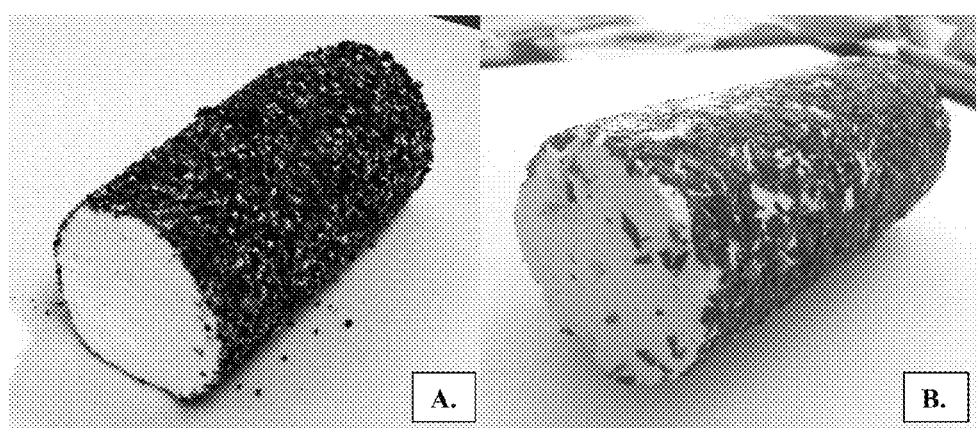
FIG. 9 shows goat cheese replicas made from non-dairy milk (A) with black pepper (B) with chives.

The goat cheese replica (FIG. 9) is now ready for packaging and shipment. Packaging includes Cryovac sealing process.

Example 7

Cultured Gels Made with Emulsions of Purified Plant Proteins and Fats

Procedure

Mixtures of purified or partially purified protein+glucose+oil were assembled and mixed with a vortex mixer to create an emulsion. Emulsions were either treated with transglutaminase (Ajinomoto Activa TI at a final concentration of 2% or 4%, as noted) or first heated to 85° C., rapidly cooled on ice and then treated with transglutaminase. Mesophilic starter culture (Danisco Choozit MA11) was added to a concentration of 0.01% (wt/vol) concomitantly with transglutaminase to allow cultures to ferment, acidify and impart flavors and aroma to the gels. Reactions were incubated overnight at 30° C. before evaluating for gel formation and aroma.

Protein Purification Methods:

All steps were carried out at 4° C. whenever possible. Centrifugation steps were at 8000 g for 20 mins, 4° C. Once fractionated, all ammonium sulfate precipitate fractions of interest were stored at −20 C until further use. Prior to their use in experiments, the precipitates were resuspended in 50 mM KPhosphate buffer pH 7.4+0.5M NaCl and dialyzed overnight against the same buffer to remove ammonium sulfate. The dialyzed solution was then centrifuged at 12000 g for 20 min to remove precipitate and then used in experiments. Protein composition at individual fractionation steps was monitored by SDS-PAGE and protein concentrations were measured by standard UV-Vis methods.

(i) Pea-albumins: Dry flour of green peas was used as a source of pea albumins. The flour was resuspended in 10 volumes of 50 mM sodium acetate buffer pH 5 and stirred for 1hr. The slurry was centrifuged at 8000 g for 20 minutes and the supernatant was collected. To this crude protein extract, solid ammonium sulfate was added to 50% saturation. The solution was stirred for 1 hour and then centrifuged. To the supernatant from this step, ammonium sulfate was added to bring to 90% saturation. After stirring for 1 hour, the solution was stirred and then centrifuged to collect the pea albumin proteins in the pellet. The pellet was stored at −20° C. until further use.

(ii) Pea-globulins: Dry green pea flour was used to extract pea globulin proteins. The flour was resuspended in 10 volumes of 50 mM KPhosphate buffer pH 8+0.4M NaCl and stirred for 1hr. After centrifugation, the supernatant was subjected to ammonium sulfate fractionation in two steps at 50% and 80% saturation. The 80% pellet containing globulins of interest was stored at −20° C. until further use.

(iii) Moong bean 8S globulins: Moong bean flour was used to extract 8S globulins by first resuspending the flour in 4 volumes of 50 mM KPhosphate buffer pH 7 (+0.5M NaCl for lab scale purifications). After centrifugation, proteins in the supernatant were fractionated by addition of ammonium sulfate in 2 steps at 50% and 90% saturation respectively. The precipitate from the 90% fraction contained the 8S globulins and was saved at −20° C. until further use.

Gel formation was tested with the following protein fractions:

(i) Pea-albumins (90% ammonium sulfate fraction from green pea dry seed flour)

(ii) Pea-globulins (80% ammonium sulfate fraction from green pea dry seed flour)

(iii) Moong bean 8S globulin (90% ammonium sulfate fraction from moong flour)

The protein solutions were dialyzed into 50 mM KPhosphate buffer pH 7-7.4+0.5M NaCl and used at concentrations between 8 mg/ml and 75 mg/ml (0.8-7.5%) as described below.

Canola oil was used to make emulsions. Stock solutions of transglutaminase (Ajinomoto) were prepared at 40% in 50 mM KPhosphate pH 7. Mesophilic starter culture (MA011 from Danisco) was used as the cheese bacterial culture; the freeze-dried culture was resuspended at a 10% in 50 mM KPhosphate buffer and used immediately in the experiments. Glucose (1%) was used as sugar source for growth of mesophilic cultures; stock solution was prepared at 40% in water.

Two conditions were used to form gels:
(i) 'Set 1': 2% protein+3% oil+4% transglutaminase; the rest water. Emulsify by vortex mixing.
(ii) 'Set 2': 7.5% protein+3% oil+2% transglutaminase; the rest water. Emulsify by vortex mixing.

Both gel compositions listed above were tested for gel formation catalyzed by transglutaminase, with and without heat denaturation of the protein component. All reactions (total volume of each, 1 ml) were first assembled in 1.5 ml micro-centrifuge tubes with protein+oil+sugar components. Emulsions were made by vortexing the samples for 30 sec. Samples to be heat denatured were immediately placed in a water bath and heated at 85° C. for 30 minutes. These samples were subsequently rapidly cooled on ice for 20 minutes. Transglutaminase and starter culture were added to all samples and mixed. Samples that formed gels upon heat/cool step were vortexed to mix the enzyme and cultures in. All samples were removed from the reaction tubes and evaluated for gel consistency and aroma after overnight incubation at 30° C.

Aroma Evaluation:

The following gels were tested for aroma (smell by 4 individuals):

Set 1: pea-albumin (heat/cool), moong (heat/cool), moong (no heat/cool),

Set 2: pea globulin (heat/cool), moong (no heat/cool)

All four individuals reported yogurt-like/fermented/sour aroma in the moong (set 1, no heat/cool) gels. They reported similar smells but to a lower degree in the moong (set 2, no heat/cool) and pea globulin (set 2, heated) gel samples. For pea-albumins (set 1, heated) and moong (set 1, heated), very faint or no aroma was reported. One of the four testers reported the aroma from moong (set 2, no heat/cool)—to be unpleasant.

Figure 10:
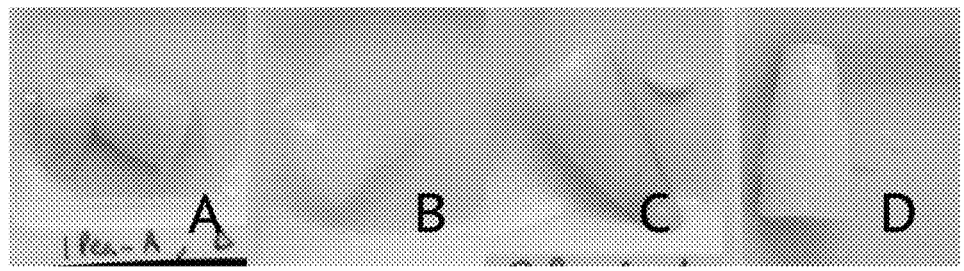
FIG. 10 shows cheese replica gels made from partially purified plant proteins and vegetable oil, cultured with mesophilic culture MA11 (Danisco): (A) depicts cultured cheese replicas made from 2% Pea albumin fraction, 3% vegetable oil, heated and crosslinked with transglutaminase; (B) depicts cultured cheese replicas made from 2% Moong bean 8S globulin fraction, 3% vegetable oil, crosslinked with transglutaminase, without prior heating; (C) depicts cultured cheese replicas made from 7.5% Pea globulin fraction, 3% vegetable oil, heated and crosslinked with transglutaminase; (D) depicts cultured cheese replicas made from 7.5% Moong bean 8S globulin fraction, 3% vegetable oil, crosslinked with transglutaminase, without prior heating of proteins.

Gel Firmness Evaluation: (FIG. 10)

'Set 1': all samples formed gels. In general these gels were weak and disintegrated easily. Pea albumins (heat/cooled) were slightly firmer in this regard.

'Set 2': All samples with exception of pea-globulins (no heat/cool) formed gels. Gels were stronger compared to Set 1 and held their shape even after removal from the tubes. Gels formed without heat/cool.

TABLE 1

MILK FORMULAS FOR SOFT FRESH, SALTED, SOFT RIPENED AND GOAT CHEESE REPLICAS

| Type of cheese replica | milk component | Amount (grams) |
|---|---|---|
| Soft fresh, salted or goat | Almond milk (per 800 ml batch). | |
| | Almond skim | 725.0 |
| | Almond Fat | 75.0 |
| | *Macadamia* nut milk (per 660 ml batch) | |
| | *Macadamia* nut skim | 328.5 |
| | *Macadamia* nut fat | 337.5 |
| Soft ripened | Almond milk (per 800 ml batch). | |
| | Almond skim | 725.0 |
| | Almond Fat | 75.0 |
| | *Macadamia* nut milk (per 660 ml batch) | |
| | *Macadamia* nut skim | 291.0 |
| | *Macadamia* nut fat | 375.0 |

TABLE 2

INGREDIENTS FOR ONE BATCH OF CHEESE REPLICA

| Ingredients | Amount (grams) |
|---|---|
| Soft Fresh Cheese Replica: | |
| Pasteurized almond milk | 800.0 |
| Pasteurized *macadamia* nut milk | 666.0 |
| Mesophilic starter culture (MA011 direct set) | 0.5 |
| Transglutaminase (900 units in 15 mls of water) | 15.0 |
| Cheese salt (internal) | 2.5 |

TABLE 2-continued

INGREDIENTS FOR ONE BATCH OF CHEESE REPLICA

| Ingredients | Amount (grams) |
|---|---|
| Salted Cheese Replica | |
| Pasteurized almond milk | 800.0 |
| Pasteurized *macadamia* nut milk | 666.0 |
| Mesophilic starter culture (MAO11 direct set) | 0.5 |
| Transglutaminase (900 units in 15 mls of water) | 15.0 |
| Soft Ripened Cheese Replica | |
| Pasteurized almond milk | 800.0 |
| Pasteurized *macadamia* nut milk | 666.0 |
| Mesophilic starter culture (MAO11 direct set) | 0.3 |
| Flora Danica | 0.2 |
| Geotrichum candidum | 0.1 |
| Penicillium candidum | 0.1 |
| Debaromyces hansenii | 0.1 |
| Transglutaminase (733 units in 15 mls of water) | 15.0 |
| Cheese salt (internal) | 4.2 |
| Goat Cheese Replica | |
| Pasteurized almond milk | 800.0 |
| Pasteurized *macadamia* nut milk | 666.0 |
| Mesophilic starter culture (MAO11 direct set) | 0.5 |
| Transglutaminase (900 units in 15 mls of water) | 15.0 |
| Cheese salt (internal) | 2.5 |
| Optional Ingredients | |
| Distilled white vinegar | 5.3 |
| Microbial "rennet:" | 0.2 |

Notes:
"Transglutaminase" here refers to Activa TI, 100 U/g, from Ajinomoto
"Mesophilic starter culture" here refers to Danisco Choozit lyophilized MA 11
"*Geotrichum candidum*" here refers to Danisco Choozit GEO17 LYO 10D
"*Debaromyces hansenii*" here refers to Chr. Hansen *Debaryomyces hansenii* LAF3
"*Flora Danica*" here refers to Chr. Hansen "*Flora Danica* freeze-dried lactic culture for direct vat set"
"*Penicillium candidum*" here refers to "*Penicillium candidum* FD PC A1" from Chr. Hansen
Microbial "rennet" here refers to FROMASE 50, protease from *Rhyzomicrobium mucor*

What is claimed is:

1. A composition comprising a non-dairy milk having at least 85% of its insoluble solids removed and a cross-linking enzyme, wherein said non-dairy milk is selected from the group consisting of almond milk, cashew milk, brazilnut milk, chestnut milk, coconut milk, hazelnut milk, macadamia nut milk, pecan milk, pistachio milk, walnut milk, and combinations thereof.

2. The composition of claim 1, wherein the cross-linking enzyme is a transglutaminase or a lysyl oxidase.

3. The composition of claim 1, wherein the cross-linking enzyme is selected from the group consisting of a transglutaminase from *Streptoverticillium mobaraense*, an enzyme similar to a transglutaminase from *Streptoverticillium mobaraense*, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), and TGM Z (TGM7).

4. The composition of claim 1, wherein the composition is free of animal proteins.

5. The composition of claim 1, wherein the composition comprises one or more of the following characteristics: a starch content less than 5% by mass, an insoluble carbohydrate content less than 5% by mass, a polysaccharide content less than 1% by mass, a polysaccharide content less than 5% by mass, a carbohydrate content less than 5% by mass, or a carbohydrate content less than 10% by mass.

6. The composition of claim 1, wherein a single monomeric or multimeric protein represents at least 80% of the protein content of the composition.

7. A composition comprising covalently crosslinked plant derived proteins, a crosslinking enzyme, and a cheese-starter culture, wherein said plant derived proteins are not soy derived, and wherein said composition is free of animal proteins.

8. The composition of claim 7, wherein the cheese-starter culture is selected from the group consisting of: a *Penicillium camemberti, Penicillium candidum, Geotrichum candidum, Penicillium roqueforti, Penicillium nalgiovensis, Verticillium lecanii, Kluyveromyces lactis, Saccharomyces cerevisiae, Candida utilis, Debaryomyces hansenii, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., *Propionibacteria* culture, and combinations thereof.

9. The composition of claim 7, wherein the cross-linking enzyme is a transglutaminase or a lysyl oxidase.

10. The composition of claim 7, further comprising oils or fats isolated from plant sources.

11. The composition of claim 9, wherein the crosslinking enzyme is selected from the group consisting of a transglutaminase from *Streptoverticillium mobaraense*, an enzyme similar to a transglutaminase from *Streptoverticillium mobaraense*, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), and TGM Z (TGM7).

12. The composition of claim 7, wherein the crosslinks are formed between glutamine and lysine side chains of respective protein constituents.

13. A cheese replica comprising a gelled emulsion of one or more cross-linked proteins derived from plants, one or more fats, a cross-linking enzyme, and a cheese-starter culture, wherein said proteins are not soy derived, and wherein said cheese replica is free of animal proteins.

14. The cheese replica of claim 13, comprising between 10% and 40% proteins from plant sources and between 0% and 65% fats from plant sources.

15. The cheese replica of claim 13, wherein the cheese replica has an insoluble carbohydrate content of less than 5% by mass.

16. The cheese replica of claim 13, wherein the cross-linking enzyme is a transglutaminase or a lysyl oxidase.

17. The cheese replica of claim 13, wherein the cheese-starter culture is selected from the group consisting of: a *Penicillium camemberti, Penicillium candidum, Geotrichum candidum, Penicillium roqueforti, Penicillium nalgiovensis, Verticillium lecanii, Kluyveromyces lactis, Saccharomyces cerevisiae, Candida utilis, Debaryomyces hansenii, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., *Propionibacteria* culture, and combinations thereof.

18. The cheese replica of claim 13, wherein said cheese-starter culture comprises *Geotrichum candidum, Penicillium candidum, Debaryomyces hansenii*, or combinations thereof.

19. The cheese replica of claim 13, wherein the one or more plant-derived proteins and one or more fats are from nuts, legumes other than soybeans, or seeds.

20. The cheese replica of claim 19, wherein the nuts comprise almonds, cashews, brazilnuts, coconuts, chestnuts, hazelnuts, macadamia nuts, pecans, pistachios, walnuts, or combinations thereof.

21. The cheese replica of claim 13, further comprising a sugar or other fermentable carbon source.

22. The cheese replica of claim 13, wherein the plant-derived proteins comprise one or more proteins selected from the group consisting of a ribosomal protein, actin, hexokinase, lactate dehydrogenase, fructose bisphosphate aldolase, phosphofructokinases, a triose phosphate isomerase, a phosphoglycerate kinase, a phosphoglycerate mutase, an enolase, a pyruvate kinase, a glyceraldehyde-3-phosphate dehydrogenase, a pyruvate decarboxylase, an actin, a translation elongation factor, ribulose-1,5-bisphosphate carboxylase oxygenase (rubisco), ribulose-1,5-bisphosphate carboxylase, an oxygenase activase (rubisco activase), an albumin, a glycinin, a conglycinin, a globulin, a vicilin, a conalbumin, a gliadin, a glutelin, a gluten, a glutenin, a hordein, a prolamin, a phaseolin (protein), a proteinoplast, a secalin, an extensin, a zein, a seed storage protein, an oleosin, a caloleosin, a steroleosin, vegetative storage protein A, vegetative storage protein B, and moong seed storage 8S globulin.

23. A cheese replica comprising
(a) almond milk,
(b) macadamia nut milk,
(c) lactic acid bacteria,
(d) a transglutaminase, and
(e) water.

24. The cheese replica of claim 23 further comprising distilled white vinegar and/or microbial coagulant.

25. The cheese replica of claim 23, further comprising salt, wherein the cheese replica is formulated as a soft fresh cheese replica or a goat cheese replica.

26. The cheese replica of claim 23, further comprising: *Penicillium camemberti, Penicillium candidum, Geotrichum candidum, Penicillium roqueforti, Penicillium nalgiovensis, Verticillium lecanii, Kluyveromyces lactis, Saccharomyces cerevisiae, Candida utilis, Debaryomyces hansensii, Rhodosporidum infirmominiatum, Candida jefer, Cornybacteria, Micrococcus* sps., *Staphylococcus, Halomonas, Brevibacterium, Psychrobacter, Leuconostocaceae, Propionibacteria*, or combinations thereof.

27. The cheese replica of claim 26, wherein the cheese replica is formulated as a soft ripened cheese replica.

28. The cheese replica of claim 23, wherein the almond milk and the macadamia nut milk are pasteurized.

29. The cheese replica of claim 23, wherein the lactic acid bacteria are selected from the group consisting of *Lactobacillus* sps., *Lactococcus, Streptococcus thermophilus*, and *Pediococcus* sps.

30. The cheese replica of claim 13, wherein the one or more plant-derived proteins and one or more fats are from almond milk or macadamia nut milk.

* * * * *